(12) United States Patent
Kim

(10) Patent No.: US 9,341,627 B2
(45) Date of Patent: May 17, 2016

(54) PROTEIN STRUCTURAL BIOMARKERS TO GUIDE TARGETED CHEMOTHERAPIES

(75) Inventor: Sunyoung Kim, Slidell, LA (US)

(73) Assignee: Sunyoung Kim, Orleans Parish ( * ) Notice: Subject to any disclaimer, the term of this patent is extended or adjusted under 35 U.S.C. 154(b) by 420 days.

(21) Appl. No.: 13/202,131

(22) PCT Filed: Feb. 19, 2010

(86) PCT No.: PCT/US2010/024777
§ 371 (c)(1),
(2), (4) Date: Oct. 24, 2011

(87) PCT Pub. No.: WO2010/096680
PCT Pub. Date: Aug. 26, 2010

(65) Prior Publication Data
US 2012/0122132 A1    May 17, 2012

Related U.S. Application Data

(60) Provisional application No. 61/154,121, filed on Feb. 20, 2009, provisional application No. 61/261,939, filed on Nov. 17, 2009.

(51) Int. Cl.
*G01N 33/574* (2006.01)
*C12Q 1/68* (2006.01)
*A61B 5/00* (2006.01)

(52) U.S. Cl.
CPC ............ *G01N 33/574* (2013.01); *C12Q 1/6886* (2013.01); *A61B 5/0059* (2013.01); *C12Q 2600/106* (2013.01); *C12Q 2600/156* (2013.01); *G01N 2800/52* (2013.01)

(58) Field of Classification Search
CPC ............... A61B 5/0059; C12Q 1/6886; C12Q 2600/106; C12Q 2600/156; G01N 33/274
USPC ........................................................ 435/18
See application file for complete search history.

(56) References Cited

PUBLICATIONS

He et al. (2013), Biophysics for therapeutic Protein Development, Ed L.O. Narhi, Biophysics for the Life Sciences, Springer Science, New York, pp. 7-31.*
Banci, L. et al., "First steps towards effective methods in exploiting high-throughput technologies for the determination of human protein structures of high biomedical value," Acta Crystallogr D Biol Crystallogr, vol. 62, pp. 1208-1217 (2006).
Barth, A. et al., "What Vibrations Tell Us About Proteins," *Q Rev Biophys*, vol. 35, No. 4, pp. 369-430 (2002).
(Continued)

*Primary Examiner* — Alexander Kim
(74) *Attorney, Agent, or Firm* — Baker Donelson; Paula Estrada de Martin

(57) ABSTRACT

A rapid, infrared spectroscopic method has been developed to assess the efficacy of targeted chemotherapeutics against the structure of the polypeptide target, based on the effect of natural polymorphic sequence variation on the conformation of the protein. This method has an advantage over the current genomics-based screening, as the new method provides a direct readout of the structural, and hence functional, outcome of polymorphisms to the protein region targeted by drugs. It allows rapid measurement of a protein's susceptibility to therapeutic targeted agents, prior to using the drug as treatment in the patient. This method can be used to identify biomarkers for a response for a protein to a drug which can be readily tested, interpreted, and used in a clinical setting.

21 Claims, 20 Drawing Sheets

(56) References Cited

PUBLICATIONS

Beckwith-Hall, B. M. et al., "Nuclear Magnetic Resonance Spectroscopic and Principal Components Analysis Investigations into Biochemical Effects of Three Model Hepatotoxins," *Chem Res Toxicol*, vol. 11, pp. 260-272 (1998).

Blagden, S. P. et al., "A phase I trial of ispinesib, a kinesin spindle protein inhibitor, with docetaxel in patients with advanced solid tumours," *Br J Cancer*, vol. 98, pp. 894-899 (2008).

Bodey, A. et al., "9-Ångström STructure of a Microtubule-Bound Mitotic Motor," *Journal of molecular biology*, vol. 388, pp. 218-224 (2009).

Brier, S. et al., "Identification of the Protein Binding Region of S-Trityl-t-cysteine, a Nw Potent Inhibitor of the Mitotic Kinesin Eg5," *Biochemistry*, vol. 43, pp. 13072-13082 (2004).

Brier, S. et al., "Use of Hydrogen/Deuterium Exchange Mass Spectrometry and Mutagenesis as a Tool to Identify the Binding Region of Inhibitors Targeting the Human Mitotic Kinesin Eg5," *Rapid Commun Mass Spectrom*, vol. 20, pp. 456-462 (2006).

Bylesjo, M. et al., "Data integration in plant biology: the O2PLS method for combined modeling of transcript and metabolite data," *Plant J*, vol. 52, pp. 1181-1191 (2007).

Carol, H. et al., "Initial Testing (Stage 1) of the Kinesin Spindle Protein Inhibitor Ispinesib by the Pediatric Preclinical Testing Program," *Pediatr Blood Cancer*, vol. 53, pp. 1255-1263 (2009).

Carter, B.Z. et al., "Regulation and Targeting of Eg5, a Mitotic Motor Protein in Blast Crisis CML: Overcoming Imatinib Resistance," *Cell Cycle*, vol. 5, No. 19, pp. 2223-2229 (2006).

Chene, P., "ATPases As Drug Targets: Learning From Their Structure," *Nature Reviews, Drug Discovery*, vol. 1, pp. 665-673 (2002).

Cochran, J. C. et al., "ATPase Mechanism of Eg5 in the Absence of Microtubules: Insight into Microtubule Activation and Allosteric Inhibition by Monastrol," *Biochemistry*, vol. 44, pp. 16633-16648 (2005).

Cochran, J. C. et al., "Monastrol Inhibition of the Mitotic Kinesin Eg5," *The Journal of biological chemistry*, vol. 280, pp. 12658-12667 (2005).

Cooper, A., et al., "Allostery With Conformational Change: A Plausible Model," *Eur Biophys J*, vol. 11, pp. 103-109 (1984).

Coureux, P. D. et al., "A Structural State of the Myosin V Motor Without Bound Nucleotide," *Nature*, vol. 425, pp. 419-423 (2003).

Cox, C. D. et al., "Kinesin Spindle Protein (KSP) Inhibitors. Part 1: The discovery of 3,5-diaryl-4,5-dihydropyrazoles as potent and selective inhibitors of the mitotic kinesin KSP," *Bioorg Med Chem Lett*, vol. 15, pp. 2041-2045 (2005).

Deavours, B. E. et al., "$Ca^{2+}$/Calmodulin Regulation of the *Arabidopsis* Kinesin-Like Calmodulin-Binding Protein," *Cell Motil Cytoskeleton* 40, 408-416 (1998).

DeBonis, S. et al., "Interaction of the Mitotic Inhibitor Monastrol with Human Kinesin Eg5," *Biochemistry*, vol. 42, pp. 338-349 (2003).

DeBonis, S. et al., "In vitro Screening for Inhibitors of the Human Mitotic Kinesin Eg5 with Antimitotic and Antitumor Activities," *Mol Cancer Ther*, vol. 3, pp. 1079-1090 (2004).

Dupuy, A. et al., "Critical Review of Published Microarray Studies for Cancer Outcome and Guidelines on Statistical Analysis and Reporting," *J Natl Cancer Inst*, vol. 99, pp. 147-157 (2007).

Fraley, M. E. et al., "Kinesin Spindle Protein (KSP) Inhibitors. Part 3: The design, synthesis, and characaterization of 2,4-diaryl-2,5 dihydropyrrole inhibitors of the mitotic kinesin KSP," *Bioorg Med Chem Lett*, vol. 16, pp. 1775-1779 (2006).

Garbaccio, R. M. et al., "Kinesin Spindle Protein (KSP) Inhibitors, Part 3: Synthesis and evaluation of phenolic 2,3-diaryl-2,5-dihydropyrroles with reduced hERG binding and employment of a phosphate prodrug strategy for aqueous solubility," *Bioorg Med Chem Lett*, vol. 16, pp. 1780-1783 (2006).

Garcia-Saez, I. et al., "Structure of Human Eg5 in Complex with a New Monastrol-based Inhibitor Bound in the R Configuration," *The Journal of biological chemistry*, vol. 282, No. 13, pp. 9740-9747 (2007).

Goormaghtigh, E. et al., "Evaluation of the Secondary Structure of apo B-100 in Low-density Lipoprotein (LDL) by Infrared Spectroscopy," *Biochimica et biophysica acta*, vol. 1006, pp. 147-150 (1989).

Gunasekaran, K., et al., "Is Allostery and Intrinsic Property of All Dynamic Proteins?" *Proteins*, vol. 57, pp. 433-443 (2004).

Hirose, K. et al., "Large Conformational Changes in a Kinesin Motor Catalyzed by Interaction with Microtubules," *Mol Cell*, vol. 23, pp. 913-923 (2006).

Hochhaus, A. et al., "Molecular and Chromosomal Mechanisms of Resistance to Imatinib (STI571) Therapy," *Leukemia* 16, 2190-96 (2002).

Hotha, S. et al., "A Potent Small-Molecule Probe for the Dynamics of Cell Division," *Angewandte Chemie (International ed)* vol. 42, pp. 2379-2382 with published supporting information (2003).

Hutchison, R. S. et al., "Confirmational Changes in the Extrinsic Manganese Stabilizing Protein Can Occur upon Binding to the Photosystem II Reaction Center: An Isotope Editing and FT-IR Study," *Biochemistry*, vol. 37, pp. 5643-5653 (1998).

Kern, D. et al., "The Role of Dynamics in Allosteric Regulation," *Current opinion in structural biology*, vol. 13, pp. 748-757 (2003).

Iakoubova, O. et al., "Association of the Trp719Arg Polymorphism in Kinesin-Like Protein 6 with Myocardial Infarction and Coronary Heart Disease in 2 Prospective Trials," *Journal of the American College of Cardiology*, vol. 51, No. 4, pp. 435-443 (2008).

Iakoubova, O. et al., "Polymorphism in KIF6 Gene and Benefit From Statins After Acute Coronary Syndromes," *Journal of the American College of Cardiology*, vol. 51, No. 4, pp. 449-455 (2008).

Jin, M. et al., "Directed evolution to probe protein allostery and integrin I domains of 200,000-fold higher affinity," *Proceedings of the National Academy of Sciences of the United States of America*, vol. 103, No. 15, pp. 5758-5763 (2006).

Jones, T. A. et al., "Improved Methods for Building Protein Models in Electron Density Maps and the Location of Errors in These Models," *Acta Cryst.*, vol. A47, pp. 110-119 (1991).

Jun, B. et al., "Millisecond time-lapsed monitoring of ATP hydrolysis by human Eg5 kinesin: real-time dynamics of conformation and chemistry in vitro," an abstract submitted to the Biophysical Society 53$^{rd}$ Annual Meeting published online Feb. 2009.

Jun, B. et al., "Real-Time structural transitions are coupled to chemical steps in ATP hydrolysis by Eg5 kinesin," a manuscript accepted by the Journal of Biological Chemistry in Feb. 2010.

Kaan, H. Y. et al., "An allosteric transition trapped in an intermediate state of a new kinesin-inhibitor complex," *Biochem J*, vol. 425, pp. 55-60 (2010).

Kabsch, W. et al., "Dictionary of Protein Secondary Structure: Pattern Recognition of Hydrogen-Bonded and Giometrical Features," *Biopolymers*, vol. 22, pp. 2577-2637 (1983).

Kim, E.D. et al., "Allosteric drug discrimination is coupled to mechanochemical changes in the Kinesin-5 motor core," a manuscript accepted by the Journal of Biological Chemistry in Feb. 2010.

Kim, S. et al.., "Conformational specificity in allosteric signaling: high-throughput measurement of modular secondary structural changes within human Eg5 kinesin," an abstract submitted to the Biophysical Society 53$^{rd}$ Annual Meeting published online Feb. 2009.

Lad, L. et al., "Mechanism of Inhibition of Human KSP by Ispinesib," *Biochemistry*, vol. 47, pp. 3576-3585 (2008).

Learman, S. S. et al., "NSC 622124 Inhibits Human Eg5 and Other Kinesins via Interaction with the Conserved Microtubule-Binding Site," *Biochemistry*, vol. 48, pp. 1754-1762 (2009).

Lin, Z. et al., "Finding Haplotype Tagging SNPs by Use of Principal Components Analysis," *Am J Hum Genet*, vol. 75, pp. 850-861 (2004).

Luo, L. et al., "ATP-competitive Inhibitors of the Mitotic Kinesin KSP That Function Via an Allosteric Mechanism," *Nat Chem Biol*, vol. 3, pp. 722-726 (2007).

Maliga, Z et al., "A Pathway of Structural Changes Produced by Monastrol Binding to Eg5," *The Journal of biological chemistry*, vol. 281, No. 12, pp. 7977-7982 (2006).

Maliga, Z. et al., "Evidence that Monastrol is an Allosteric Inhibitor of the Mitotic Kinesin Eg5," *Chemistry & biology*, vol. 9, pp. 989-996 (2002).

(56) References Cited

OTHER PUBLICATIONS

Maliga, Z. et al., "Small-molecule and Mutational Analysis of Allosteric Eg5 Inhibition by Monastrol," *BMC Chem Biol*, vol. 6, No. 2, pp. 1-9 (2006).
Mayer, T. U. et al., "Small Molecule Inhibitor of Mitotic Spindle Bipolarity Identified in a Phenotype-Based Screen," *Science*, vol. 286, pp. 971-974 (1999).
Misra, J. et al., "Interactive Exploration of Microarray Gene Expression Patterns in a Reduced Dimensional Space," *Genome Res*, vol. 12, pp. 1112-1120 (2002).
Monod, J. et al., "On the Nature of Allosteric Transitions: A Plausible Model," *Journal of molecular biology* 12, 88-118 (1965).
Parke, C. L. et al., "ATP Hydrolysis in Eg5 Kinesin Involves a Catalytic Two-water Mechanism," *The Journal of biological chemistry*, vol. 285, No. 8, pp. 5859-5867 (2010).
Parke, C.L. et al., "Crystal structure of HsEg5 in complex with S-trityl-L-cysteine," an abstract submitted to the Biophysical Society 53$^{rd}$ Annual Meeting published online by Feb. 2009.
Paschou, P. et al., "PCT-Correlated SNPs for Structure Identification in Worldwide Human Populations," *PLoS Genet*, vol. 3, Iss. 9, pp. 1672-1686 (2007).
Pasinelli, P. et al., "Molecular Biology of Amyotrophic Lateral Sclerosis: Insights from Genetics," *Nature Reviews Neuroscience*, vol. 7, pp. 710-723. (2006).
Rath, A. et al., "Detergent binding explains anomalous SDS-PAGE migration of membrane proteins," *Proceedings of the National Academy of Sciences of the United States of America*, vol. 106, pp. 1760-1765 (2009).
Reubold, T. F. et al., "A Structural Model for Actin-Induced Nucleotide Release in Myosin," *Nature structural biology*, vol. 10, pp. 826-830 (2003).
Shiffman, D. et al., "A Kinesin Family Member 6 Variant is Associated with Coronary Heart Disease in the Women's Health Study," *Journal of the American College of Cardiology*, vol. 51, No. 4, pp. 444-448 (2008).
Shah, N.P. et al., "Multiple BCR-ABL Kinase Domain Mutations Confer Polyclonal Resistance to the Tyrosine Kinase Inhibitor Imatinib (STI571) in Chronic Phase and Blast Crisis Chronic Myeloid Leukemia," *Cancer Cell*, vol. 2, pp. 117-125 (2002).
Skoufias, D. A., et al., "S-Trityl-L-cysteine Is a Reversible, Tight Binding Inhibitor of the Human Kinesin Eg5 That Specifically Blocks Mitotic Progression," *The Journal of biological chemistry*, vol. 281, pp. 17559-17569 (2006).
Sunder-Plassmann, N. et al., "Synthesis and biological evaluatiojn of new tetrahydro-β-carbolines as inhibitors of the mitotic kinesin Eg5," *Bioorg Med Chem*, vol. 13, pp. 6094-6111 (2005).

Surewicz, W. K. et al., "Determination of Protein Secondary Structure by Fourier Transform Infrared Spectroscopy: A Critical Assessment," *Biochemistry*, vol. 32, No. 2, pp. 389-394 (1993).
Susi, H. et al., "Resolution-Enhanced Fourier Transform Infrared Spectroscopy of Enzymes," *Methods in Enzymology*, vol. 130, pp. 290-311 (1986).
Turner, J. et al., "Crystal Structure of the Mitotic Spindle Kinesin Eg5 Reveals a Novel Conformation of the Neck-linker," *The Journal of biological chemistry*, vol. 276, No. 27, pp. 25496-25502 (2001).
Wojcik, E. J. et al., "Disparity in Allosteric Ineractions on Monastrol with Eg5 in the Presence of ADP and ATP: A Difference FT-IR Investigation," *Biochemistry*, vol. 43, No. 31, pp. 9939-9949 (2004).
Yan, Y. et al., "Inhibition of a Mitotic Motor Protein: Where, How, and Conformational Consequences," *Journal of molecular biology*, vol. 335, pp. 547-554 (2004).
Zhang, B. et al., "Crystal structure of *Hs*Eg5 in complex with clinical candidate CK0238273 provides insight into inhibitory mechanism, potency, and specificity," *Biochem Biophys Res Commun*, vol. 372, pp. 565-570 (2008).
Barth, Andreas et al., "What vibrations tell us about proteins," Quarterly Rev of Biophysics, vol. 35, No. 4, pp. 369-430 (2002).
Gunasekaran, K. et al., "Is Allostery an Intrinsic Property of *All* Dynamic Proteins?" Proteins: Structure, Function, and Bioinformatics, vol. 57, pp. 433-443 (2004).
Kern, Dorothee et al., "The role of dynamics in allosteric regulation," Curr.Opin. in Struc. Biology, vol. 13, pp. 748-757 (2003).
Kong, Jilie et al., "Fourier Transform Infrared Spectroscopic Analysis of Protein Secondary Structures," Acta Biochimica et Biophysica Sinica, vol. 39, No. 8, pp. 549-449 (2007).
Kuriyan, John et al., "The origin of protein interactions and allostery in colocalization," Nature, vol. 450, pp. 983-990 (2007).
Arley, Frédéric Arley et al., "A Molecular Marker of Artemisinin—Resistant *Plasmodium falciparum* Malaria," Nature, vol. 505, pp. 50-67 (2014).
Fenwick, R. Bryn et al., "Correlated motions are a Fundamental Property of β-sheets," Nature Communications, pp. 1-9 (2014).
Masetti, Matteo et al., "Protein Dynamics of the HIF-2α PAS-B Domain upon Heterodimerization and Ligand Binding," PLOS One, vol. 9, iss. 4, pp. 1-13 (2014).
Tolonen, Ellen et al., "Allosteric Transition and Binding of Small Molecule Effectors Causes Curvature Change in Central β-sheets of Selected Enzymes," J. Mol. Model, vol. 17, pp. 899-911 (2011).
Wojcik, Edward J. et al., "Disparity in Allosteric Interactions of Monastrol with Eg5 in the Presence of ADP and ATP: A Difference FT-IR Investigation," Biochemistry, vol. 43, No. 31, pp. 9939-9949 (2004).

* cited by examiner

*N-Terminal L5 mutants*

US 9,341,627 B2

PROTEIN STRUCTURAL BIOMARKERS TO GUIDE TARGETED CHEMOTHERAPIES

This is the United States national stage of international application PCT/US2010/024777, international filing date Feb. 19, 2010, which claims the benefit of the filing dates of provisional U.S. application Ser. No. 61/154,121, filed 20 Feb. 2009, and of provisional U.S. application Ser. No. 61/261,939, filed 17 Nov. 2009, under 35 U.S.C. §119(e).

This invention was made with government support under grant number GM066328 awarded by the National Institutes of Health. The government has certain rights in this invention.

TECHNICAL FIELD

This invention pertains to a spectroscopic method to assess the efficacy of chemotherapeutics targeted to a specific protein in a patient, based on the effect of polymorphic sequence variation on the conformation pattern of the protein. This method views the structure of polypeptides and develops protein biomarkers that can be used to predict the protein's (and thus the patient's) response to a drug treatment. Using this method, protein biomarkers can be screened in individual patients to determine which patients will benefit from a particular drug therapy or to correctly tailor the dose of a drug and limit unnecessary toxicity.

BACKGROUND ART

Today's health practitioners are encouraged to diagnose and treat patients based on individual genetic composition. Pharmacogenomics promises to establish how genetic variation affects the way individuals will respond to drugs. Translation of this information into clinical settings would provide physicians the tools for selecting an optimal treatment for individual patients. Importantly, differences in drug responses caused by genetic differences among individuals could be correlated or quantified by diagnostic testing of an individual prior to receiving a particular drug or amount. The drug and amount could thus be tailored to the individual. Biomarker tests are currently based on polymorphic alleles at the genetic and protein level. For example, Oncotype DX is a commercially available test that predicts breast cancer recurrence and is used as a treatment guide for chemotherapy for breast cancer.

Pharmacogenomics research focuses primarily on establishing correlations between microarray gene expression profiles and disease states, often without defining biochemical pathways and mechanisms. This strategy is widely adopted, easy to automate, and scalable to high-throughput modes. However, the reliability of microarray biomarker assays for disease is unknown with few effective biomarkers or tools for assessment established. For example, only one assessment has begun to be used in oncology practice.

Efforts to identify cancer biomarkers through genomic methods have included use of microarray assays to mine for genetic predictors of therapeutic response and to mine for variations in tumor gene expression in patients whose disease later exhibits different degrees of aggressive behavior. These biomarkers are defined not by classical single markers, but by sets of genes whose up- or down-regulation in expression is correlated with a therapeutic response or aggressive behavior of the disease. Many of the gene signatures generated in the last five years for predicting disease have had only marginal overlap with those identified in the original studies, even though subsequent work had corroborated pathway mechanisms in the model organism studies. For example, BCR-ABL kinase domain mutations have been found to confer resistance to the tyrosine kinase inhibitor imatinib, a competitive inhibitor for the substrate ATP (60,61,62). As used herein and in the claims, a "drug" or "drug compound" is a therapeutic compound that is given to a patient that targets a specific protein.

Minimizing problems of validity, reproducibility, and bias in biomarker generation and employment is imperative when searching for predictors of therapeutic response. There is a need for standardization in methods and technology platforms to define biomarkers for predicting disease progression as well as predicting response. The interaction of a targeted protein and its inhibitor drug can be useful. In particular, certain enzymes such as ATPases and kinases that use ATP as a substrate have showed potential as targets for drugs. ATPases are enzymes that use ATP hydrolysis to achieve a cellular function, and are involved in various human diseases. Kinases will transfer the phosphate group in ATP to another compound. As such, ATPases and kinases are important protein targets for therapeutic drugs. In the ATPases, most of the drugs have inhibited activity by binding to an allosteric site. Examples include, Kinesin (Eg5) and its inhibitor monastrol used for cancer therapy; muscle myosin II and its inhibitor N-benzyl-p-toluene sulphonamide used for muscle relaxation; $Na^+,K^+$-ATPase and the inhibitor digoxin used for heart failure; P glycoprotein and its inhibitor XR9576 used for cancer, $H^+,K^+$-pump and its inhibitor benzimidazoles used for gastric ulcers; vacuolar $H^+$-ATPase and the inhibitor bafilomycin A1 used for osteroporosis; and DNA topoisomerase II and the inhibitor ICRF-193 used for cancer (59).

Allostery is important in controlled catalysis, signal transduction, and apoptosis (1). The classic view of proteins demonstrating this property (2) asserts that binding of a ligand at one site provokes conformational changes at a remote, second site. Recent studies (3) evaluating underlying mechanisms of allostery alternatively suggest that ligand binding results in selection of pre-existing conformational substrates. Implicit in the latter model, interactions between the orthosteric and allosteric sites are tightly linked through structure and thermodynamics (4).

The human Kinesin-5 motor protein (Eg5 or KSP) plays key roles in bipolar mitotic spindle formation and is a protein target for allosteric compounds (5-7) that alter catalytic ATPase activity of the protein (8,9). There are many compounds and classes of compounds that are know to inhibit KSP including monastrol, S-trityl-L-cysteine and its derivatives, quinazolines (e.g., ispinesib), adociasulfates, thetrahydroishquinolines, dihydropyrazoles, thiophenes, pyrrolotriazines, thiazoles, gossypol, indoles, and biphenyls. The best-characterized inhibitors, monastrol (10) and S-trityl-L-cysteine [STC; (9)], were uncovered from independent chemical screens. Biochemical studies demonstrate a wide concentration range of inhibition by these compounds (10-12) differences in the kinetic mechanism of allostery (13-15), and even allosteric activation (16) is possible.

Interest in these allosteric compounds, monastrol and STC, has been acute as they are potential anticancer agents. Additionally, these compounds serve as research tools to probe the fundamental mechanism by which Eg5, and perhaps all other motor proteins, convert and transduce energy to conformational changes in distal regions of the protein. Insights concerning allosteric conformational states of Eg5 result principally from diffraction- and microscopy-based techniques. The kinesin motor domain is an arrowhead-shaped structure with a central β-sheet flanked by 3 helices on each side. In crystallographic studies of Eg5·ADP complexed with monastrol (17,18) and other allosteric inhibitors (12,19-21), the wildtype Kinesin-5 motor domain displays a similar conformer, irrespective of the chemical nature of the allosteric drug.

The most notable conformational change observed is the adoption of a 'closed' conformation by the insertion loop (L5) of α2 helix that cradles the allosteric compound. This is in contrast with the 'open' conformation observed in the absence (22) of an allosteric ligand. However, conformational transitions of the L5 loop are found not only in response to drug binding, but also in normal motor function. The Eg5 conformer trapped by allosteric agents is suggested to be an intermediate state of its normal ATP hydrolysis cycle (23). The L5 loop is observed in the 'closed' conformation in cryo-EM experiments (24) with a *D. melanogaster* homologue of Eg5 bound to microtubules using non-hydrolyzable substrate analogues and in Eg5·AMPPNP crystals in the absence of allosteric agents (25).

No consensus of L5 residues key for transmitting allosteric information has been established, primarily due to interdependence of the allosteric and active-site interactions and the lack of rapid methods to observe structures of mutant motor proteins. Simple sequence conservation analysis does not reveal how the L5 loop specifically recognizes and binds an allosteric molecule. Studies (15,17,26,27) using targeted mutagenesis to measure the contribution of specific contacts in Eg5 allostery and chemical-kinetic measurements of mutant motor ensembles in solution on the whole concluded that their data were consistent with the crystallographic observation of the wildtype Eg5·inhibitor complexes. Yet, neither these reports nor X-ray structural analyses of allosterically-inhibited Eg5 proteins arrive at a common set of contact residues for binding many different chemical partners.

The advent of the structural genomics era has led to the curation of many motor protein structures; to date, 20 RCSB Protein Data Bank (PDB) entries for wildtype Eg5 alone have been deposited. (See the website: www dot rcsb dot org/pdb/home/home dot do) Although the atomic level detail of the structures is fairly complete, whether these static 'snapshots' accurately reflect functional states that these amino acid assemblies can achieve is more difficult to determine. Thus, obtaining all needed conformational possibilities in kinesin mechanotransduction and its allosteric inhibition is a significant challenge.

DISCLOSURE OF INVENTION

I have developed an infrared spectroscopic method to assess the efficacy of targeted chemotherapeutics against the structure of the polypeptide target based on the effect of natural polymorphic sequence variation on the conformation of the protein. This method has an advantage over the current genomics-based screening, as the new method provides a direct readout of the structural, and hence functional, outcome of polymorphisms to the protein region targeted by drugs. Second, it allows rapid measurement of tumor protein susceptibility to therapeutic targeted agents, prior to using the drug as treatment in the patient. Third, this method can be used to identify biomarkers for a response for a protein to a drug which could be readily tested, interpreted, and used in a clinical setting.

For an example of the above discovery, the human Kinesin-5 protein (Eg5 or KSP), essential in mitosis, was used. Eg5 is known to be a target for >80 classes of allosteric compounds that bind to a surface-exposed site formed by the L5 loop. Ligand-bound states of two L5-directed inhibitors against wildtype and 15 Kinesin-5 mutants were compared by ATPase assays and Infrared (IR) spectroscopy. Biochemical kinetics uncovered functional differences between individual residues at the N- or C-termini of the L5 loop. Infrared evaluation of solution structure and multivariate analysis of the vibrational spectra uncovered changes in L5-localized $3_{10}$-helix and disordered content, regardless of substitution or drug potency. Coupled to these local structural events are two types of rearrangements in β-sheet hydrogen-bonding. Drug potency was correlated with these transformations in β-sheet contacts and was corroborated by wildtype Kinesin-5 crystal structures. These data directly show that mutation and/or ligand binding can not only remodel the allosteric binding surface but also transmit long-range effects. These findings prove that these relatively rapid IR approaches can find and identify structural biomarkers that can be used in a determination of drug sensitivity and drug efficacy.

The invention provides a method for predicting the probable response of a patient to a drug compound; wherein the patient has a disease; wherein the drug compound inhibits a protein that is associated with the disease; and wherein the protein is polymorphic in the population, such that there is substantial variation in the responsiveness of the disease to the drug compound between individuals as a result of such polymorphism; said method comprising the steps of: (a) determining whether the variant of the protein expressed by the patient has greater spectroscopic similarity to: (i) a variant of the protein that is known to be responsive to the drug compound, in the absence of the drug compound, or (ii) a complex of the known-responsive-variant of the protein bound to the drug compound; and (b) predicting that the patient will likely be responsive to the drug compound if there is greater spectroscopic similarity to (i); or predicting that the patient will likely be unresponsive or less responsive to the drug compound if there is greater spectroscopic similarity to (ii); wherein the degree of spectroscopic similarity is determined as infrared absorption or transmittance at one or more wavelengths at which there is a significant difference in absorption or transmittance between (i) and (ii).

In the method given above, the determination of the variant of a protein expressed by the patient can be conducted by direct spectroscopic measurement of protein expressed by the patient. In particular, such determination can be made by genetic analysis of the patient's DNA or RNA encoding the protein, and comparing the patient's allele or alleles for the protein to those of one or more reference samples for which direct spectroscopic measurements of the protein have previously been conducted. Any spectroscopic method that measures molecular vibrations at different frequencies can be used, e.g., infrared spectroscopy or Raman spectroscopy. A preferred method is Fourier-transform infrared spectroscopy is useful.

This method can be used for patients with cancer or other diseases, and with drugs targeted to the specific disease, such as chemotherapeutic agents. One such chemotherapeutic agent would be one that acts as an allosteric inhibitor of the protein. One such protein that can be targeted is the kinesin Eg5 protein. Two known drugs that inhibit mitosis by inhibition of the Eg5 protein are monastrol and S-trityl-L-cysteine (STC).

BRIEF DESCRIPTION OF THE DRAWINGS

FIG. 11D illustrates the results of the wildtype Eg5 and Eg5 proteins with sustitutions at the A133 residue, as described in Table 1, as analyzed by SDS-PAGE using a 10% acrylamide gel.

FIG. 4B shows wildtype as inhibited by both monastrol in 1:1 (black box, dark grey fill) and 1:20 (black box, mid grey fill) ratios and STC (light grey box, dot fill). FIG. 4C shows mutant E116 polymorphisms as compared to wildtype. FIG. 4D shows mutant E118 polymorphisms as compared to wildtype.

FIG. 5B shows wildtype as inhibited by both monastrol in 1:1 and 1:20 ratios and STC (light grey box, dot fill). FIG. 5C shows mutant D130 polymorphisms as compared to wildtype. FIG. 5D shows mutant A133 polymorphisms as compared to wildtype.

MODES FOR CARRYING OUT THE INVENTION

Figure 1A:
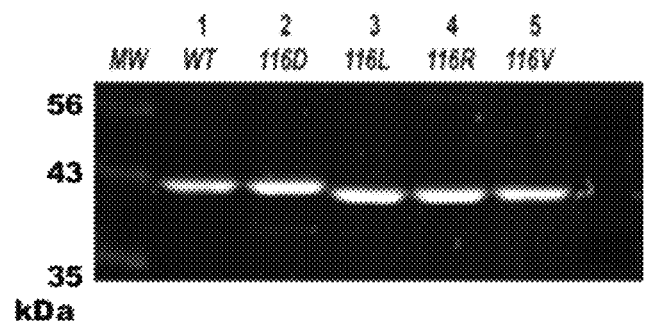
FIG. 1A illustrates the results of the wildtype Eg5 and Eg5 proteins with sustitutions at the E116 residue, as described in Table 1, as analyzed by SDS-PAGE using a 10% acrylamide gel. The gel migration of the double-mutant, E116D/E118D (DD), matched wildtype Eg5 samples (data not shown).

I have shown that the efficacy of targeted chemotherapeutics against the structure of polypeptide targets can be directly assessed through a pioneering high-throughput, specialized implementation of vibrational spectroscopy. The final cellular target for clinical drugs is typically polypeptides but correlations between protein structure and therapeutic outcome are commonly unknown. There are no reports of a rapid and quantitative method for assaying conformational alterations resulting from peptide sequence variations. This lack of information has hampered translation of gene signatures into clinical diagnostics. Here I have found protein spectroscopic signatures that reflect conformational ensembles adopted in solution and that can be used as clinical biomarkers that can improve treatment decisions.

Using this method, the efficacy of targeted chemotherapeutics for patients can be predicted, potentially even in a quantitative manner, based on the polymorphic variant of the targeted protein in the individual and based on the effect of this polymorphic sequence variation on protein conformation. This method is unique on three fronts. First, protein conformation has an advantage over genomics-only-based evidence, as it provides a direct readout of the structural, and hence functional, outcome of polymorphisms to the actual target protein for drugs. Second, this method allows rapid measurement of a target protein's susceptibility to therapeutic agents, rather than deciphering treatment effectiveness from long-term observation of disease progression. Third, a single biomarker for response of a protein target to a drug, independent of tumor state or stage, is readily testable, interpretable, and amenable to translating into clinical application, compared to complex, multivariable signatures of gene or protein networks.

Clinicians, for the first time, will be able to reliably predict which individual patients will benefit from a particular drug treatment, to correctly tailor dosages, and to limit unnecessary toxicity, based on rapid assessment of drug-to-target interactions. Most cancer treatments at present benefit only a minority of patients to whom they are administered, and this over-treatment of patients is a major expense for society. A second aspect of this work is that structural screening of target proteins may be extendable to established linkages between polymorphisms and drug efficacy for patients with neurodegenerative or heart diseases.

One embodiment of this invention is to focus on treatment to traditional cytotoxic drugs that affect rapidly dividing cells in general, and uses small-molecule inhibitors specific for the deregulated proteins of cancer cells. These deregulated proteins are often enzymatic domains that are typically mutated and/or overexpressed specifically in cancer cells. Oncological protein targets catalyzing nucleotide triphosphate hydrolysis, such as kinesin motor proteins and tyrosine kinases, are examples of such proteins. These protein families share a common catalytic capacity of hydrolyzing adenosine triphosphate (ATP).

Protein kinases use one of the products of ATP hydrolysis to phosphorylate protein substrates, and thereby trigger signal transduction cascades in cells. These enzymes regulate multiple processes that contribute to tumor development and progression, including cell growth, differentiation, migration, and apoptosis. For human tumors whose growth is driven by these activated kinases, targeted drugs, such as imatinib (Gleevec), can inhibit or reverse malignant progression. In contrast, kinesin motor proteins utilize the energy from ATP breakdown to move along or destabilize microtubules. Essential for cell division, the clinical and oncogenic role of kinesin spindle protein (KSP) in mitosis has been demonstrated by a number of groups: (i) inhibition of KSP leads to apoptotic cell death and (ii) KSP is preferentially over-expressed in malignant cells, but not normal non-dividing cells such as terminally differentiated neurons. From the >80 chemical classes of KSP inhibitors reported, five compounds, including ispinesib, are under active clinical development by pharmaceutical companies.

I have developed a high-throughput method toward analyzing protein structure using FTIR in solution. In this post-genomic era, hundreds of protein variants can be produced cheaply and quickly. It has been much less straightforward to screen or select for protein structure: X-ray crystallography, NMR spectroscopy, and even CD spectroscopy are not amenable to high-throughput approaches. The protein secondary structure can be monitored by Fourier-transform infrared (FTIR) spectroscopy. The amide I', or C=O stretching, IR vibration of the peptide bond is sensitive to the hydrogen bonding patterns of differing secondary structure elements and depends on the solution structure of proteins.

I have developed a high-throughput measurement of solution structure with the motor domain of the human kinesin spindle (KSP) protein. The motor domain of the human KSP is the 'business end' of the kinesin molecule: it contains the binding sites for ATP and microtubules. It also provides several experimental advantages when compared to other proteins: (i) it is a relatively small protein that can be produced in large quantities (15-60 mg KSP/L culture) using recombinant expression systems; (ii) basal ATPase activity is readily measured in high-throughput format; and (iii) such systems are amenable to efficient site-directed mutagenesis and crystallization.

As shown below, IR measurements were used to discover a structural biomarker that can be used for biophysical profiling of polymorphisms at the protein level. More than half of the mutants examined had catalytic rates comparable or greater than wildtype samples. I predict that patients with seemingly normal Eg5 function can harbor a polymorphism that would confer resistance to clinical drugs. The method described herein using the structural biomarker screen can help an oncologist find the best inhibitor for the Eg5 of a specific patient.

This invention uses vibrational spectroscopy to monitor protein structure biomarkers to predict drug efficacy for targeted chemotherapeutic agents. Although these biophysical methods are low resolution, in comparison to x-ray crystallography or NMR spectroscopy, the experimental advantage is its realization in high-throughput modes. There is no parallel approach to microarray genetic profiling that can probe protein structure. Results from conformational profiling will allow the scientific community to evaluate subtle as well as pleiotropic effects to protein structure upon amino acid substitution and build a large database of conformational states to query additional scientific questions. For example, this method could assist in optimizing patient selection for clinical trials: individuals who were found to be resistance to the test drug in a prescreen could be eliminated from the trial and data obtained on remaining patients would be a truer representation of the trial drug efficacy. In addition, such biophysical profiling of kinesin conformational ensembles, shown below, may be extendable to the other kinesin proteins, such as Kif5A, Kif21A, and Kif1B, in which polymorphisms have been demonstrated to result in neurodegenerative conditions, and Kif6 in acute coronary syndromes. (55,56,57,58)

One embodiment of this new method is on chemotherapeutic inhibitors such as allosteric inhibitors that target specific proteins of cancer cells, e.g., the use of monastrol on human kinesin Eg5 (also known as KSP or kinesin spindle protein). The first step is to assay in vitro conformational signatures of the purified protein by vibrational spectroscopy, e.g., by using Fourier-transform infrared (FTIR) spectroscopy; comparison of the 1700-1600 cm⁻ region of the infrared spectrum from wildtype protein alone and from wildtype protein bound to an inhibitor will detect changes in wild-type protein secondary or tertiary structure due to the binding of the inhibitor. Then using the same technique, protein with a known polymorphism can be assayed for secondary or tertiary structure changes. I have found that variant proteins that are resistant to the inhibition of the drug often show secondary or tertiary structural changes similar to those seen in wildtype proteins when bound to the chemotherapeutic drug, e.g., as revealed by alterations in the IR spectrum. The variant proteins were resistant to inhibition because their secondary or tertiary structure was already similar to that of the "inhibited" state, even though the proteins may not be functionally inhibited. Tumors with these variant proteins would not be affected by treatment with the chemotherapeutic drug. Thus using vibrational spectroscopy, the efficacy of treating a certain tumor in a patient with a chemotherapeutic drug that targets a specific tumor protein can be assayed quickly prior to treatment.

One example is the differing efficacies in drug inhibition of Eg5. Without wishing to be bound by this theory, I believe that there is more than one pathway for allosteric communication that initiates from the L5 loop of Eg5: differences in the inhibitory power of monastrol and STC amongst the Kinesin-5 orthologues thus result from these deviations in allosteric communication. Biochemical behavior of mutant proteins has been measured as well as the protein secondary structure in solution. The resulting model reveals that allosteric conformational changes at the protein surface can promote two different types of intraprotein contacts at the central core of the kinesin motor domain. These changes discriminate between the inhibitory power of these allosteric drugs.

Example 1

Materials and Methods

Generation of Single- and Double-Mutants of Eg5.

Starting cDNA was the truncated form of wildtype Eg5 as previously reported [residues 1-370; (28)]. Appropriate primers were synthesized and used for site-directed mutagenesis with the QuikChange II XL kit (Stratagene, La Jolla, Calif.). Construction of the Eg5 motor domain with substitutions of Asp for E116 and E118 was performed using two rounds of mutagenesis. Expected mutations were confirmed by a single-read sequencing reaction. A subset of five mutations was completely sequenced on both strands to ensure that inadvertent coding errors were not introduced. The mutations produced are shown below in Table 1.

Motor Protein Expression and Purification.

The wildtype Eg5 kinesin motor domain, as well as single- and double-site polymorphisms, were expressed in BL21-Codon Plus (DE3)-RIL cell lines (Stratagene) and purified by cation exchange chromatography as previously described (28). Purity of wildtype and all Eg5 substitutions were determined by SDS-PAGE analysis using a 10% acrylamide-0.27% bisacrylamide gel, with a 0.38 M Tris-HCl, pH 8.8 resolving and a 0.125 M Tris-HCl, pH 6.8 stacking gel components. SDS sample buffer was added, adjusting the sample to a final concentration of 2% SDS, 0.29 M 2-mercaptoethanol, 0.05 M Tris-HCl pH 6.8, 10% glycerol, 0.0025% (w/v) bromophenol blue. SDS-PAGE samples were then boiled at 100° C. to ensure denaturing conditions. Following boiling, samples were immediately run along an unstained molecular weight ladder (New England Biolabs, Mass.) and were visualized using Sypro Tangerine (Molecular Probes, Oreg.). Protein purity was estimated to be >90%. All protein concentrations were determined by Bradford assay (Coomassie Plus Protein Assay Reagent, ThermoScientific, Massachusetts), using bovine serum albumin (BSA) as the standard; concentrations ranged from 0.5-6.0 mg/mL. Final storage buffer for the purified Eg5 proteins was 125 mM NaCl, 50 mM HEPES pH 7.4, 0.1 mM MgATP, 1 mM DTT and 10% glycerol. Purified motor protein was flash-frozen in liquid nitrogen and stored at −80° C. until use. Unless otherwise indicated, all chemical compounds were purchased from Sigma-Aldrich (St. Louis, Mo.).

In Vitro ATPase Assays.

Basal ATPase activities were measured with a coupled enzymatic assay as previously described (29) with 5 μM motor protein and 1 mM MgATP in a SpectraMax 2E spectrophotometer for high-throughput kinetic measurements as previously described (30). Reactions were supplemented with monastrol (0-600 μM; Sigma-Aldrich, St. Louis, Mo.) or S-trityl-L-cysteine (STC; 0-200 μM; Sigma-Aldrich, St. Louis, Mo.) as appropriate, and control reactions contained equivalent dimethyl sulfoxide (DMSO). Reactions used for calculation of the $IC_{50}$ values contained between 5 and 22.5 mM NaCl. Data were reproducible with protein samples purified from differing batches of cultured cells from two different laboratories.

Infrared Spectroscopy.

All spectroscopic data were acquired at room temperature as previously described (28) on a Vertex 80v (Bruker Optics, Billerica, Mass.) with the use of a BioATR (Bruker Optics, Billerica, Mass.). The spectrometer was equipped with a liquid nitrogen-cooled MCT (mercury cadmium telluride) cryo-detector or photovoltaic detector and a KBr beam splitter. The mirror velocity was 20 kHz, the spectral resolution was 2 cm⁻¹, and 1000 mirror scans were acquired for each double-sided interferogram. A 6 mm aperture, gain of 1 on the preamp A setting, Blackman-Harris 3-Term apodization function, and two levels of zero-filling were used. A minimum of 3 spectra and two independent protein purifications per Eg5 sample were used to generate the averaged data.

Protein samples were $^2H_2O$-exchanged using Zeba desalting spin columns (Pierce, Rockford, Ill.) or SpectraPor dialysis membranes (Spectrum Laboratories, California) and equilibrated with $^2H_2O$ buffer (10 mM HEPES p$^2$H 7.4, 0.5 mM $MgCl_2$, and 0.1 mM MgATP). Protein samples utilized in IR experiments had final concentrations of 0.9-5 mg/ml, as determined by Bradford assays. Stock concentrations of monastrol and STC were 100 mM in 100% DMSO. Note that positive displacement pipettes were used for all DMSO aliquotting to ensure accurate volumetric measurement of the viscous solvent. For Eg5·inhibitor samples, a 20 µl sample was achieved by mixture of 19 µl of Eg5 protein with 1 µl of inhibitor in equimolar concentrations, resulting in a final DMSO concentration of 5%. Inhibitor stocks were serially diluted in DMSO, using a maximum 1:5 ratio, until the desired concentration was achieved. Of this 20 µl mixture, a sample volume of 12-15 µl was dispensed onto the ATR crystal and allowed to equilibrate to room temperature for 10-15 minutes before an interferogram was collected.

Spectral Analyses.

Each sample spectrum was subtracted from the spectrum of $^2H_2O$ buffer or $^2H_2O$ buffer plus DMSO when samples contained drug. After baseline correction, spectra were area normalized. Savitsky-Golay second-derivative, Fourier self-deconvolution, and spectral fitting analysis were performed with Grams/AI (ThermoFischer Scientific, Massachusetts). Self-deconvolution was performed with a Bessel apodization function and peak fitting utilized the Levenberg-Marquardt method with Lorentzian components. Identical parameters were used for all spectra with an amide I' fitting range of 1710 $cm^{-1}$ to 1594 $cm^{-1}$. Bandwidth, frequency, and amplitude of each spectral component were iterated until a minimum in the fit to the experimental data was obtained. The frequencies of the resulting spectral components and their amplitudes generated good fits, as judged by residuals and reduced $\chi^2$ parameters.

The frequencies, obtained from the second-derivative and Fourier self-deconvolution analyses, were used as the first set of inputs for the multivariate data analyses. Area-normalized data sets of infrared spectra, in comparison to wildtype Eg5 samples, also were used as the second set of inputs for the multivariate data analyses. Principal component analysis (PCA) was performed with Matlab software (Mathworks, Mass.). PCA plots presented were scaled on x- and y-axis [0,1]. The point spread on the PCA indicated that the infrared measurements sample the variances in vector space, and there is high signal-to-noise in the infrared spectra and calculations. All figures were generated using IGOR Pro software (Wavefunction, Oreg.).

Crystallization and X-Ray Structure Solution.

The Eg5 motor domain (residues 1-369) was expressed in bacteria and purified as previously described (25). Prior to crystallization experiments, purified Eg5 (~250 µM) was mixed with 1 mM STC (Sigma Aldrich). Original crystals obtained in 250 mM $NH_4SO_4$, 25% PEG 3350, 100 mM MES pH 6.0, and 10 mM trimethylamine hydrochloride were used to streak seed crystals grown in 250 mM $NH_4SO_4$, 25% PEG 3350, 100 mM MES pH 6.0, 10 mM trimethylamine hydrochloride, and 10-15% glycerol. Crystals were grown at 4° C. in sitting drops consisting of 2 µl of protein/drug mixture and 1 µl of well solution. Cubic crystals appeared several days after streak seeding. The crystals were allowed to grow for several weeks before being flash frozen for data collection. Diffraction data were collected at 100K using a Bruker Microstar X-ray generator equipped with Helios optics and a Proteum 4K Platinum 135 CCD camera and were integrated and scaled with PROTEUM2 software (Bruker AXS). Crystals belonged to space group I2(1)3 with cell parameters of a=b=c=157.93 Å. The Eg5·STC complex structure was determined via molecular replacement methods (AMoRe) using a search model based on molecule A of the Eg5·ADP·monastrol complex (PDB ID 1x88). Successive rounds of manual model building as previously described (31) and automated refinement were performed using O and CNS. The final model was refined to R and $R_{free}$ values of 24.07 and 27.46, respectively (All |F|>0; 25.0-2.5 Å), and contained residues 18-271 and 288-366, along with the Mg-ADP complex, 74 waters, one STC molecule, and one trimethylamine molecule.

Example 2

Substitutions of L5 Residues Result in Altered SDS-PAGE Mobility

The initial step of this study was to assess how perturbations of the L5 loop affect Eg5 steady-state kinetics and solution structure. The first type of perturbation involves alteration of sidechain chemistry. Fifteen (15) mutations were sampled at four sites in the L5 loop: two at the N-terminus and two at the C-terminus of the insertion loop. Prior studies scrutinizing the allosteric pocket typically assumed that point mutations have little effect beyond the localized change of a particular functional group. However, this stance can underestimate the ability of the point mutation to remodel the binding surface or transmit long-range effects that are dependent on the nature of the substitution. Therefore, the mutations used herein ranged from conservative to pleiotropic alterations; this allowed a wider range of chemical and structural outcomes at specific positions to be seen.

The N-terminal residues chosen were E116 and E118. The E116 sidechain is oriented inwards toward the allosteric pocket, in contrast to the E118 sidechain orientation toward the orthosteric site. C-terminal L5 residues studied were D130 and A133, embedded within short stretches of negatively-charged and hydrophobic sidechains and interrupted by a proline. There was no apparent interaction between the sidechains of any of these four residues and the allosteric inhibitors in co-crystal structures. However, the E116V and E118N substitutions are present in the Drosophila Kinesin-5 protein that is insensitive to allosteric inhibitors and that the D130V and A133D mutations were found in human cell lines resistant to Eg5 allosteric inhibitors (16).

Figure 1B:
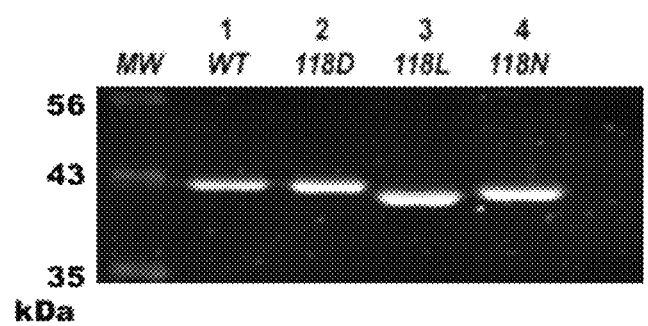
FIG. 1B illustrates the results of the wildtype Eg5 and Eg5 proteins with sustitutions at the E118 residue, as described in Table 1, as analyzed by SDS-PAGE using a 10% acrylamide gel.
Figure 1C:
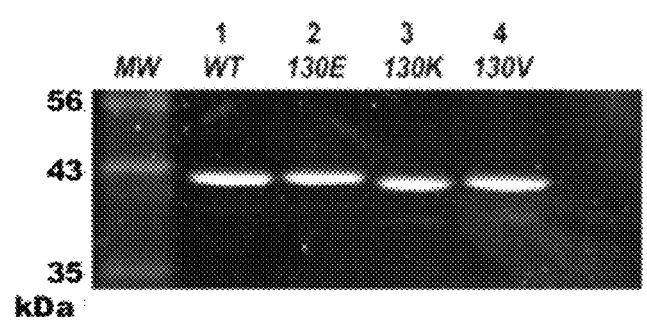
FIG. 1C illustrates the results of the wildtype Eg5 and Eg5 proteins with sustitutions at the D130 residue, as described in Table 1, as analyzed by SDS-PAGE using a 10% acrylamide gel.
Figure 1D:
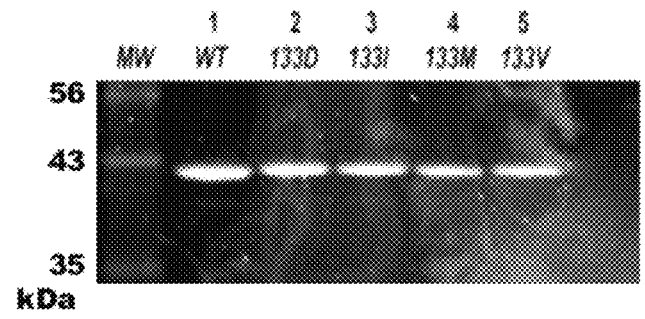

Expression plasmids with these and other substitutions in Eg5 cDNA were successfully constructed, and the mutant motor proteins were readily expressed and purified, as evident from SDS-PAGE (FIGS. 1A-1D). The location and amino acid substitutions for the mutant proteins in FIGS. 1A-D are shown in Table 1. Wildtype Eg5 has an apparent and expected molecular weight of 42 kDa. Migration of the mutant Eg5 proteins in SDS-polyacrylamide gel electrophoresis, however, does not correlate with calculated molecular weights. Both forms of anomalous gel mobility are observed for mutant proteins. Faster migration of purified proteins is detected for nonconservative substitutions of the L5 carboxylates (FIGS. 1A and 1B). C-terminal mutant proteins overall have slower gel mobility in SDS-PAGE (FIGS. 1C and 1D).

TABLE 1

Location and Amino Acid in L5 Loop of Human Eg5

| Name-Location in Eg5 | Wildtype (WT)/ Mutation (M) | Amino Acid |
|---|---|---|
| A. N terminal at 116 location | | |
| E116 | WT | Glutamic Acid |
| E116D | M | Aspartic Acid |
| E116L | M | Lysine |
| E116R | M | Arginine |
| E116V | M | Valine |
| B. N terminal at 118 location | | |

TABLE 1-continued

Location and Amino Acid in L5 Loop of Human Eg5

| Name-Location in Eg5 | Wildtype (WT)/ Mutation (M) | Amino Acid |
|---|---|---|
| E118 | WT | Glutamic Acid |
| E118D | M | Aspartic Acid |
| E118L | M | Leucine |
| E118N | M | Asparagine |
| C. C terminal at 130 location | | |
| D130 | WT | Aspartic Acid |
| D130E | M | Glutamic Acid |
| D130K | M | Lysine |
| D130V | M | Valine |
| D. C terminal at 133 location | | |
| A133 | WT | Alanine |
| A133D | M | Aspartic Acid |
| A133I | M | Isoleucine |
| A133M | M | Methionine |
| A133V | M | Valine |

The observed gel shift behavior of Eg5 mutant proteins originates in altered detergent binding in the L5-modified proteins. A recent study (50) demonstrates that PAGE migration, SDS aggregation number, hydrodynamic radius and protein conformation are all directly linked. Observed variations in gel shifting in FIGS. 1A-1D suggested that more than one type of modification in intra-protein contacts can be found in these mutant Eg5 motor domains and that affect the overall protein fold of the altered motor domains.

Example 3

Figure 2A:
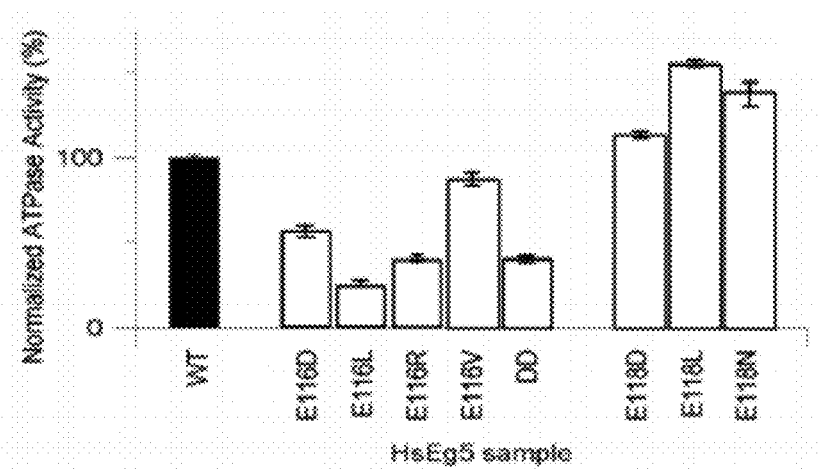
FIG. 2A illustrates the normalized ATPase activity expressed as a percent of wildtype for the mutant proteins for E116 and E118 as described in Table 1. Shown are steady-state, basal ATP hydrolysis rates, for which mean $V_{max}$ for WT (black) is $0.144\pm0.003$ s$^{-1}$. For WT, n=101, while n for all substitutions ranges from 20-51. DD represents the double mutant E116D-E118D. All reactions contain 3-15 mM NaCl.

Preservation of N-Terminal Local Structure and C-Terminal Chemistry in the L5 Loop are Required for Allostery and Catalysis There are marked kinetic differences between the N-terminal and C-terminal substitutions of L5 loop residues. Compared with wildtype samples, single-site substitutions of E116 decreased the steady-state, basal ATP hydrolysis rate of Eg5 kinesin monomers (FIG. 2A, open boxes). However, mutants of E118 displayed increased activity (FIG. 2A, filled boxes). These results were consistent, whether or not the amino acid substitutions were synonymous with carboxylates. These data demonstrated that the native interactions of E116 and/or E118 in the motor domain influence ATP hydrolysis rates achievable by Eg5. Moreover, for mutants of these two positions in the L5 loop, the faithful difference in mutant kinetic behavior, despite conservative or pleiotropic changes, implicated the native sidechain of these N-terminal L5 residues not primarily in electrostatic interactions, but rather predominantly structural roles, likely propagating effects to the nucleotide site.

Figure 2B:
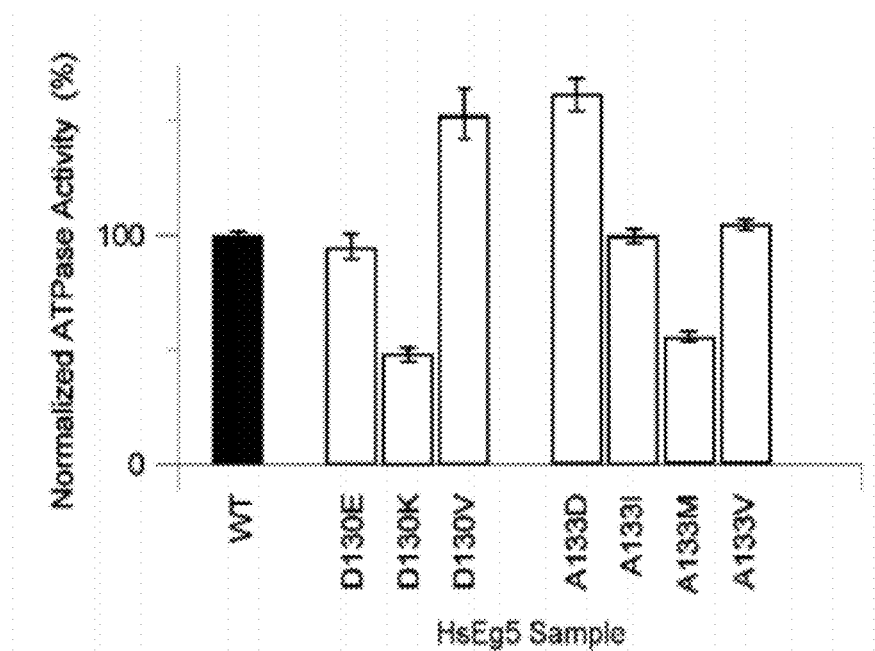
FIG. 2B illustrates the normalized ATPase activity expressed as a percent of wildtype for the mutant proteins for D130 and A133 as described in Table 1. Shown are steady-state, basal ATP hydrolysis rates, for which mean $V_{max}$ for WT (black) is $0.144\pm0.003$ For WT, n=101, while n for all substitutions ranges from 20-51. All reactions contain 3-15 mM NaCl.

In contrast, the single-site C-terminal L5 substitutions did not have such uniform kinetic outcomes: rates of ATP hydrolysis for these residues were dependent on sidechain chemistry (FIG. 2B). For both D130 and A133, substitutions can result in either increased or decreased ATPase activity. D130E samples showed similar basal rates to wildtype Eg5 protein. Substitution of a positively-charged sidechain in lieu of aspartate at residue 130 decreased Eg5 activity, whereas replacement with a hydrophobic sidechain increased basal rates by approximately 50%. A133I and A133V Eg5 motor domains had ATP hydrolysis rates comparable to wildtype samples, but A133M was not as kinetically active. Only the substitution of a polar, charged sidechain for A133 produced an increase in enzymatic activity. Mutations, known to confer ispinesib-resistance (32,33), have opposing changes in chemical character and have the greatest change in basal rates. Therefore, the chemical nature of these C-terminal L5 residues is key in their catalytic role.

Figure 2C:
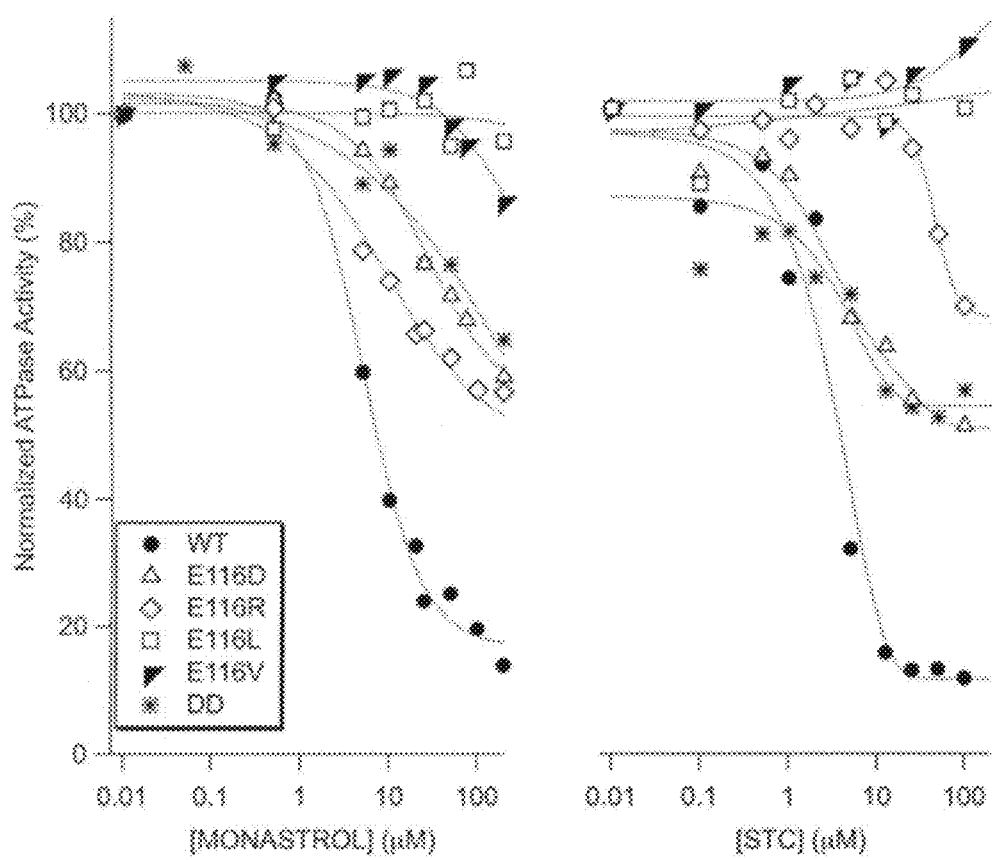
FIG. 2C illustrates a plot of normalized Eg5 ATP hydrolysis rates for E116 mutants against increasing concentrations of monastrol (left panels) or STC (right panels). WT kinetic data (black or grey) are superimposed on E116. ATP hydrolysis rates for each substitution are normalized with respect to the 0 mM monastrol or 0 mM STC measurements of the parent substitution. All data points in the figure reflect the averaged normalized rate of at least 3 independent trials and 2-4 separate protein preps and the standard error.
Figure 2D:
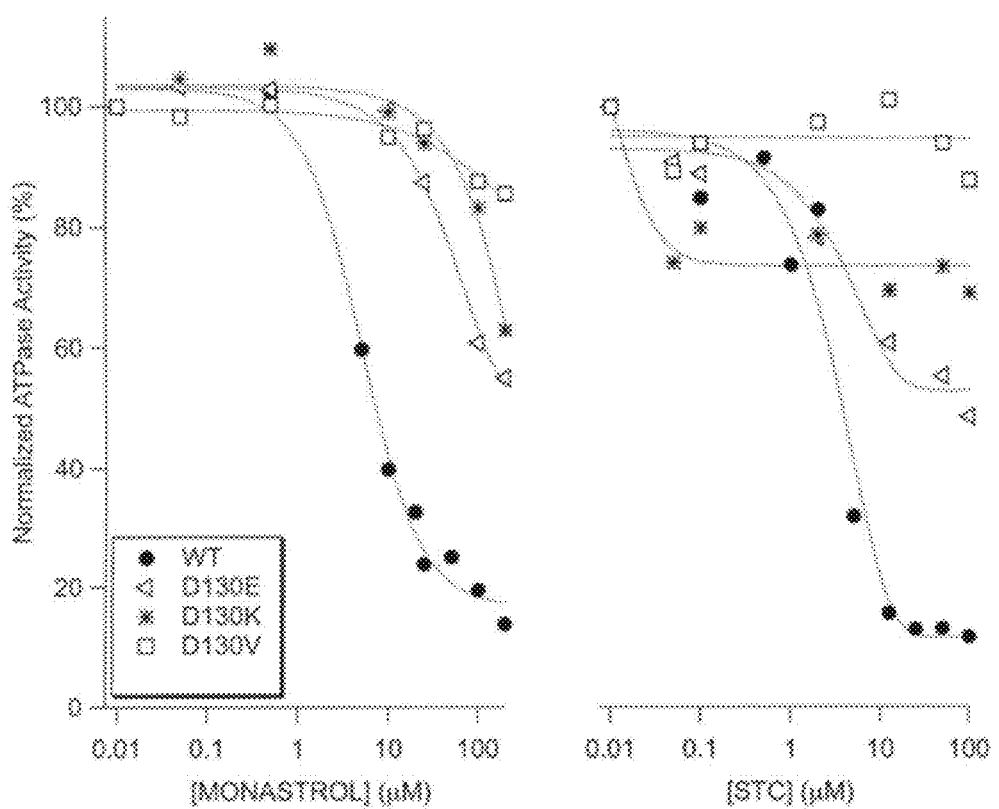
FIG. 2D illustrates a plot of normalized Eg5 ATP hydrolysis rates for D130 mutants against increasing concentrations of monastrol (left panels) or STC (right panels). WT kinetic data (black or grey) are superimposed on D130. ATP hydrolysis rates for each substitution are normalized with respect to the 0 mM monastrol or 0 mM STC measurements of the parent substitution. All data points in the figure reflect the averaged normalized rate of at least 3 independent trials and 2-4 separate protein preps and the standard error.
Figure 2E:
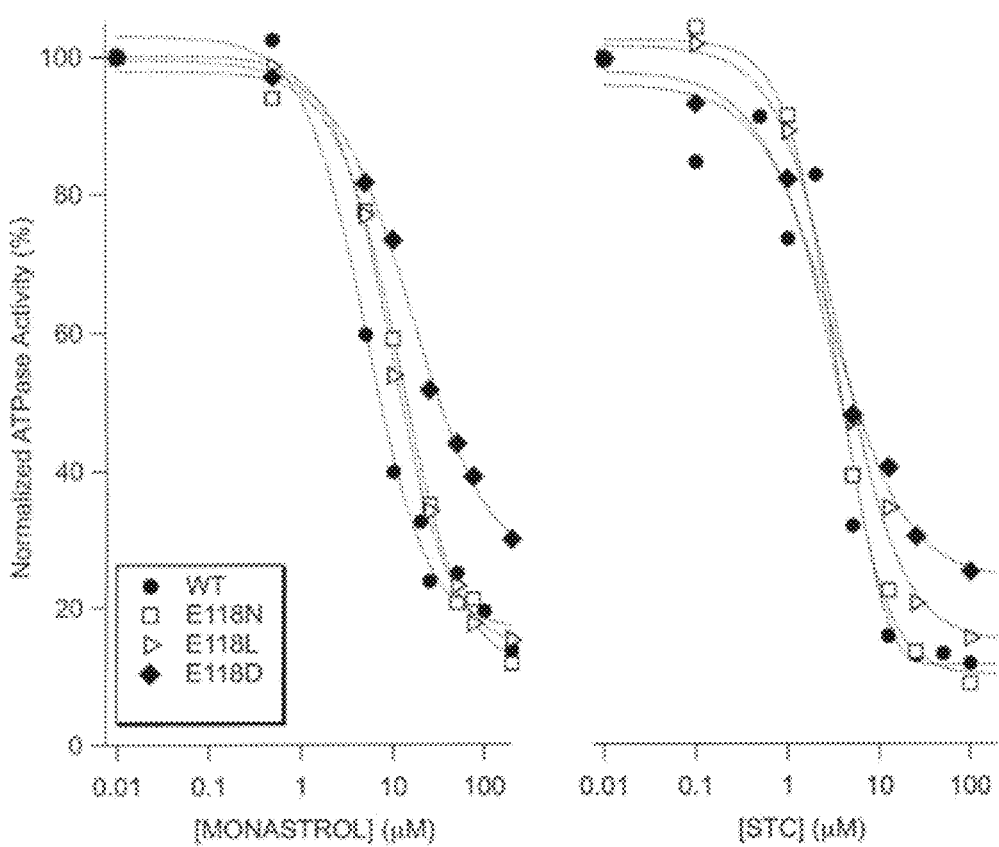
FIG. 2E illustrates a plot of normalized Eg5 ATP hydrolysis rates for E118 mutants against increasing concentrations of monastrol (left panels) or STC (right panels). WT kinetic data (black or grey) are superimposed on E118. ATP hydrolysis rates for each substitution are normalized with respect to the 0 mM monastrol or 0 mM STC measurements of the parent substitution. All data points in the figure reflect the averaged normalized rate of at least 3 independent trials and 2-4 separate protein preps and the standard error.

The second type of perturbation to the L5 loop was use of allosteric small-molecule inhibitors. Specifically, the effects of two commonly-used inhibitors of Eg5, monastrol and S-trityl-L-cysteine were examined. Wildtype Eg5 had an $IC_{50}$ of 8 and 4 µM for monastrol and STC, respectively (black filled circles, FIG. 2C). Altering the chemistry of the E116, E118, D130, and A133, despite the paucity of direct contacts observed in crystal structures, changed the effect of small-molecule ligands on Eg5, encompassing the kinetic range from neutral to inhibited. For E118 substitutions (FIG. 2E), all variants of Eg5 were allosterically inhibited in equivalent measure to wildtype protein, suggesting that this carboxylate sidechain is not involved in allosteric inhibition.

Figure 2F:
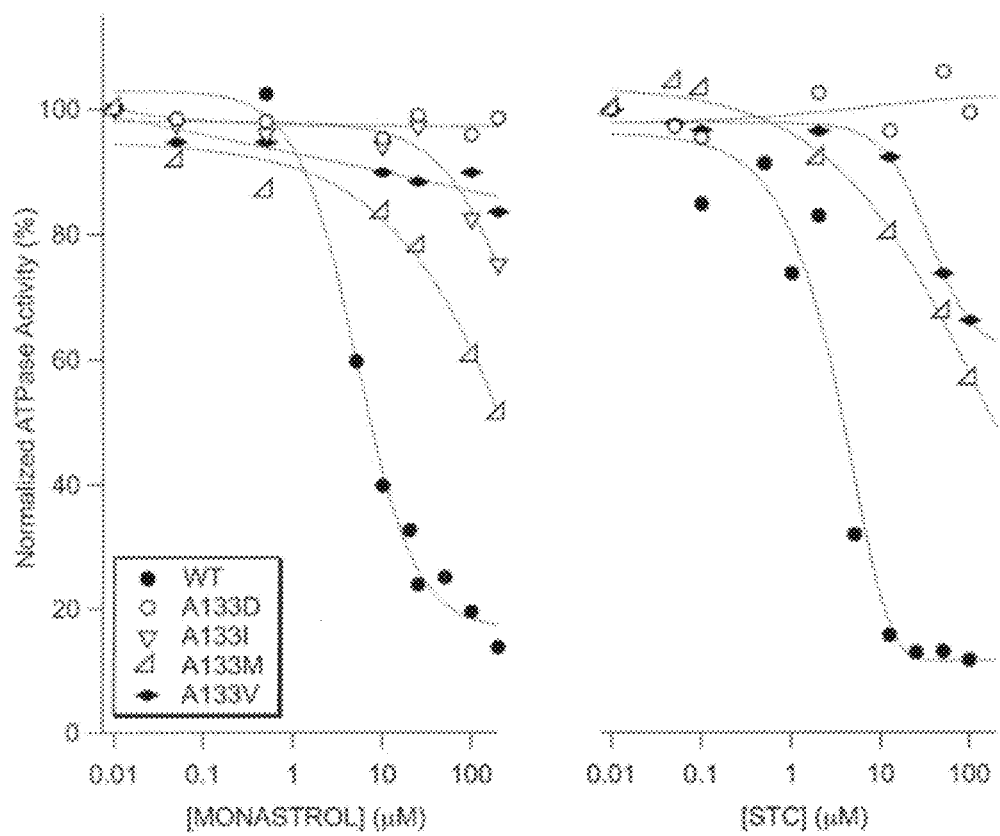
FIG. 2F illustrates a plot of normalized Eg5 ATP hydrolysis rates for A133 mutants against increasing concentrations of monastrol (left panels) or STC (right panels). WT kinetic data (black or grey) are superimposed on A133. ATP hydrolysis rates for each substitution are normalized with respect to the 0 mM monastrol or 0 mM STC measurements of the parent substitution. All data points in the figure reflect the averaged normalized rate of at least 3 independent trials and 2-4 separate protein preps and the standard error.

In general, N-terminal mutations had a strong, positive correlation between loss of basal rate and loss of drug sensitivity, while C-terminal mutations did not have a clear relationship. All E116 (FIG. 2C), D130 (FIG. 2D), and A133 (FIG. 2F) mutants showed reduced sensitivity to monastrol and STC but to varying degrees. Only the E116R and D130K motor proteins displayed differing levels of inhibition between the two compounds used, the former being more sensitive to monastrol and the latter to STC. Of the C-terminal L5 mutants, D130V and A133D were the most insensitive to either inhibitor, as anticipated from studies on ispinesib (16). For the N-terminal L5 substitutions, loss of allosteric compound sensitivity was more marked in samples with aliphatic residue substitutions at positions 116 of the L5 loop, compared to Eg5 proteins with charged residues at these positions. Thus, the capacity for hydrogen-bond formation and the sidechain length of E116 are important for basal catalytic activity and for effective allosteric inhibition of Eg5.

Example 4

Secondary Structural Changes of L5-Perturbed Kinesins in Solution can be Quantitatively and Rapidly Measured by Infrared Spectroscopy To understand the role protein structure plays in allosteric interactions, conformational transitions throughout a globular protein need to be monitored in response to localized perturbations. There are no published structural descriptions of Eg5 mutants. Crystallographic reports of how allosteric small-compounds perturb wildtype Eg5·ADP complexes (19, 20,34,35) note conformational changes in the L5 loop, but no pronounced changes in the nucleotide pocket or in other regions of the motor domain. Although X-ray diffraction of protein crystals provides detailed atomic information, it can only provide a static single frame, or 'snapshot' of Eg5 inhibition.

Methods for determining the protein structure in solution can provide an ensemble conformational picture of polypeptides in a near-native environment. However, to date, there is no published method, rapid and quantitative, for screening conformational alterations resulting from peptide sequence variations that parallels high-throughput measurement of kinetic activity or genetic microarray profiling (36). Thus, there is a need to develop high-throughput methods to analyze protein structure in solution. Infrared spectroscopy is widely used as a technique for the analysis of protein secondary structure (37). The spectral region most commonly examined is the amide I band, centered at 1650 $cm^{-1}$, which arises from the delocalized C=O vibrations of the peptide linkage. Changes in the amide I region can be directly correlated with variation in the percentage of protein occupied in α-helix, β-sheet, or other structural motifs. Infrared data on Eg5 proteins in solution were obtained using reflectance spectral acquisition methods: spectra were collected using only 12-15 µL volumes and 20 min of time.

Figure 3A:
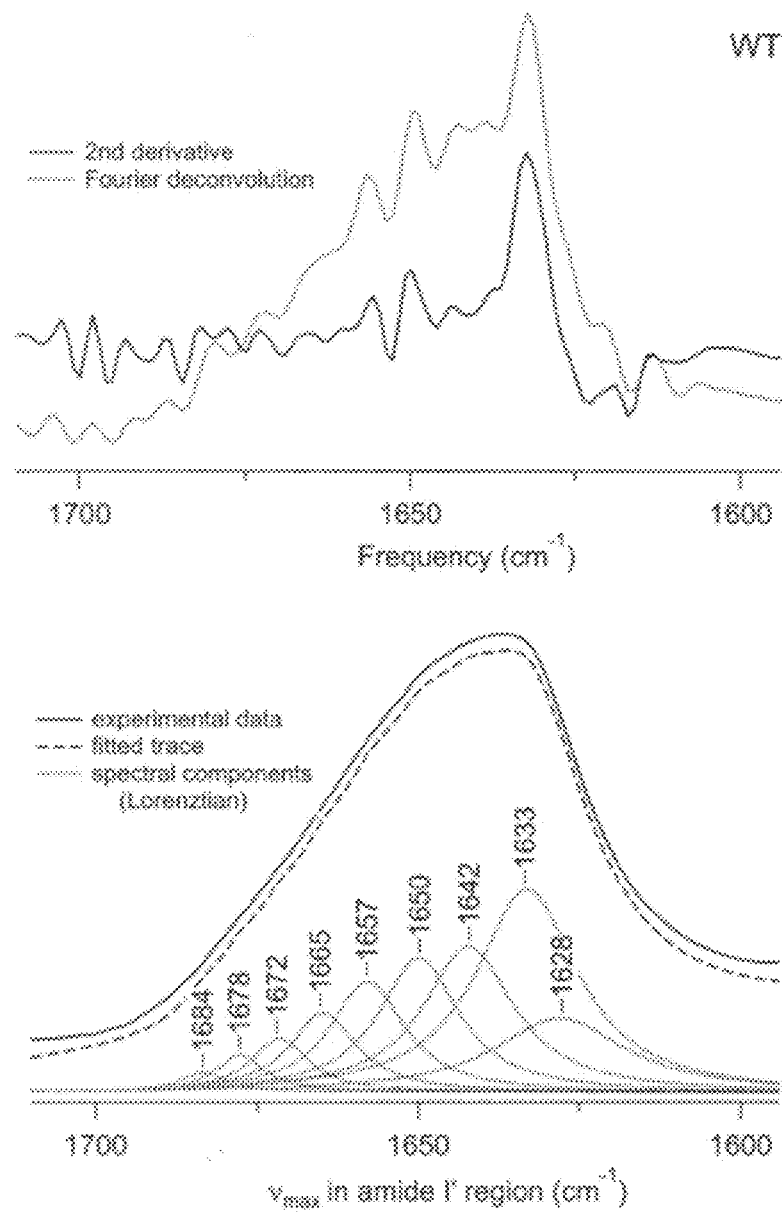
FIG. 3A illustrates the method of band narrowing and regression analysis for wildtype $2^{nd}$ derivative (solid), Fourier deconvolution (dashed), and peak fit calculations. The amide I' band of the averaged FTIR spectra (solid) is superimposed with the fitted trace (dashed light grey). Areas under the Lorenztian components were compiled and wildtype subtracted to result in spectrotype profiles of the structural data. Frequencies of the spectral components for all spectra were centered and binned to $\pm2$ wavenumbers.
Figure 3B:
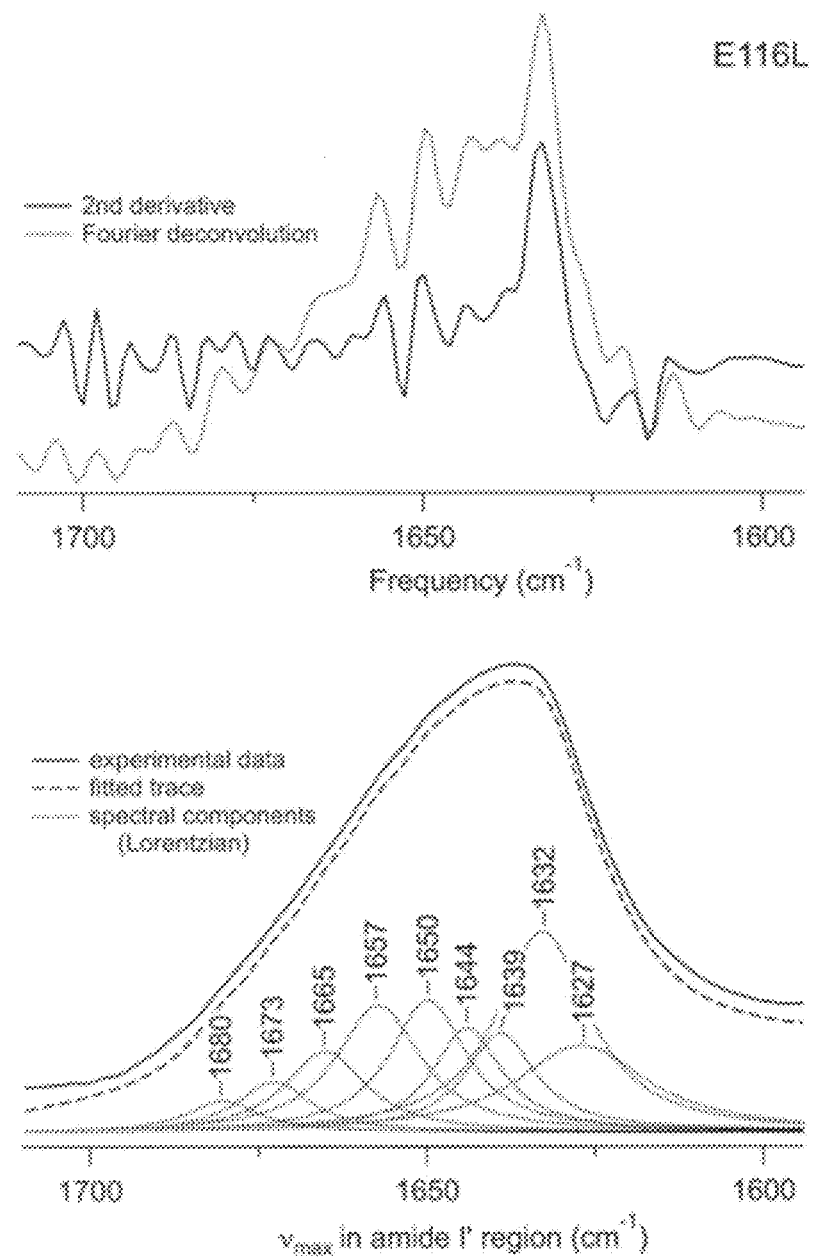
FIG. 3B illustrates the method of band narrowing and regression analysis for E116L mutant $2^{nd}$ derivative (solid), Fourier deconvolution (dashed), and peak fit calculations. The amide I' band of the averaged FTIR spectra (solid) is superimposed with the fitted trace (dashed light grey). Areas under the Lorenztian components were compiled and wildtype subtracted to result in spectrotype profiles of the structural data. E116L showed a loss at 1684 and a gain at 1644. Frequencies of the spectral components for all spectra were centered and binned to $\pm2$ wavenumbers.
Figure 3C:
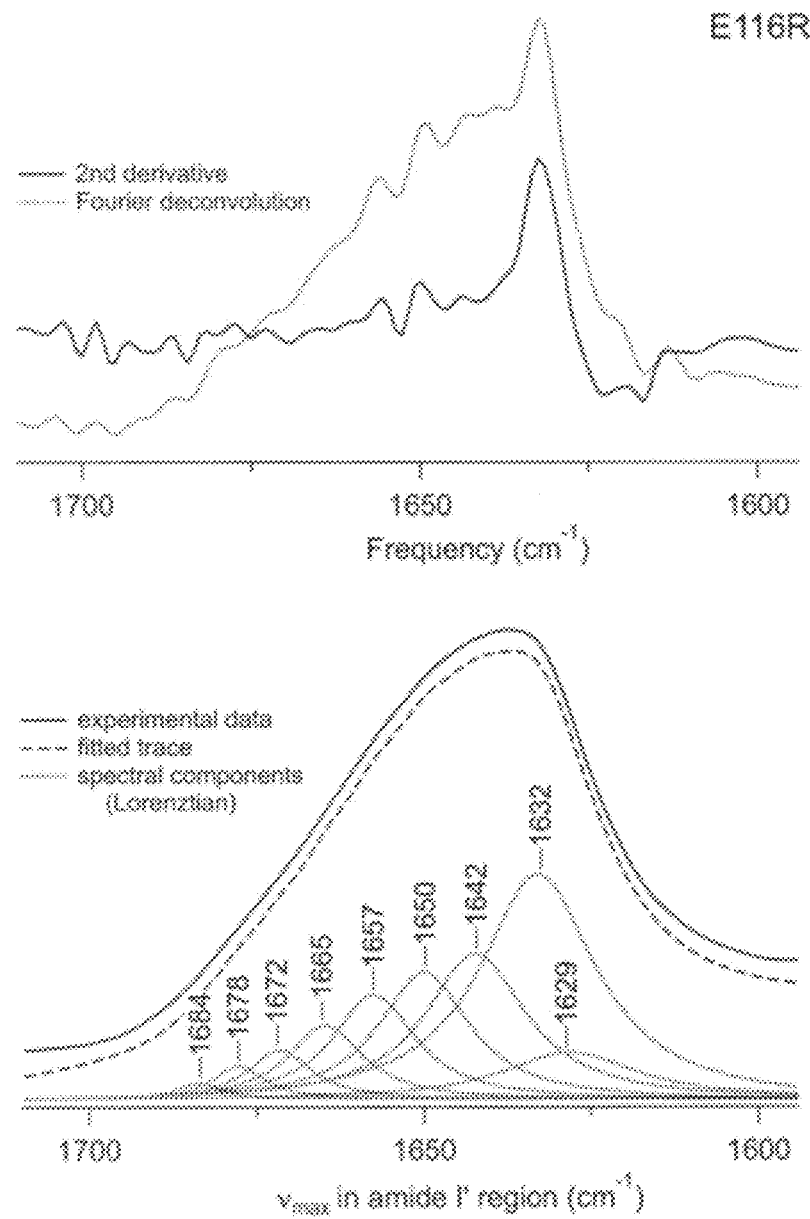
FIG. 3C illustrates the method of band narrowing and regression analysis for E116R mutant $2^{nd}$ derivative (solid), Fourier deconvolution (dashed), and peak fit calculations. The amide I' band of the averaged FTIR spectra (solid) is superimposed with the fitted trace (dashed light grey). Areas under the Lorenztian components were compiled and wildtype subtracted to result in spectrotype profiles of the structural data. Band narrowing of E116R resulted in Lorentzians centered at the same frequencies as WT. Both do not contain a 1646 Lorentzian component. Frequencies of the spectral components for all spectra were centered and binned to $\pm2$ wavenumbers.
Figure 4A:
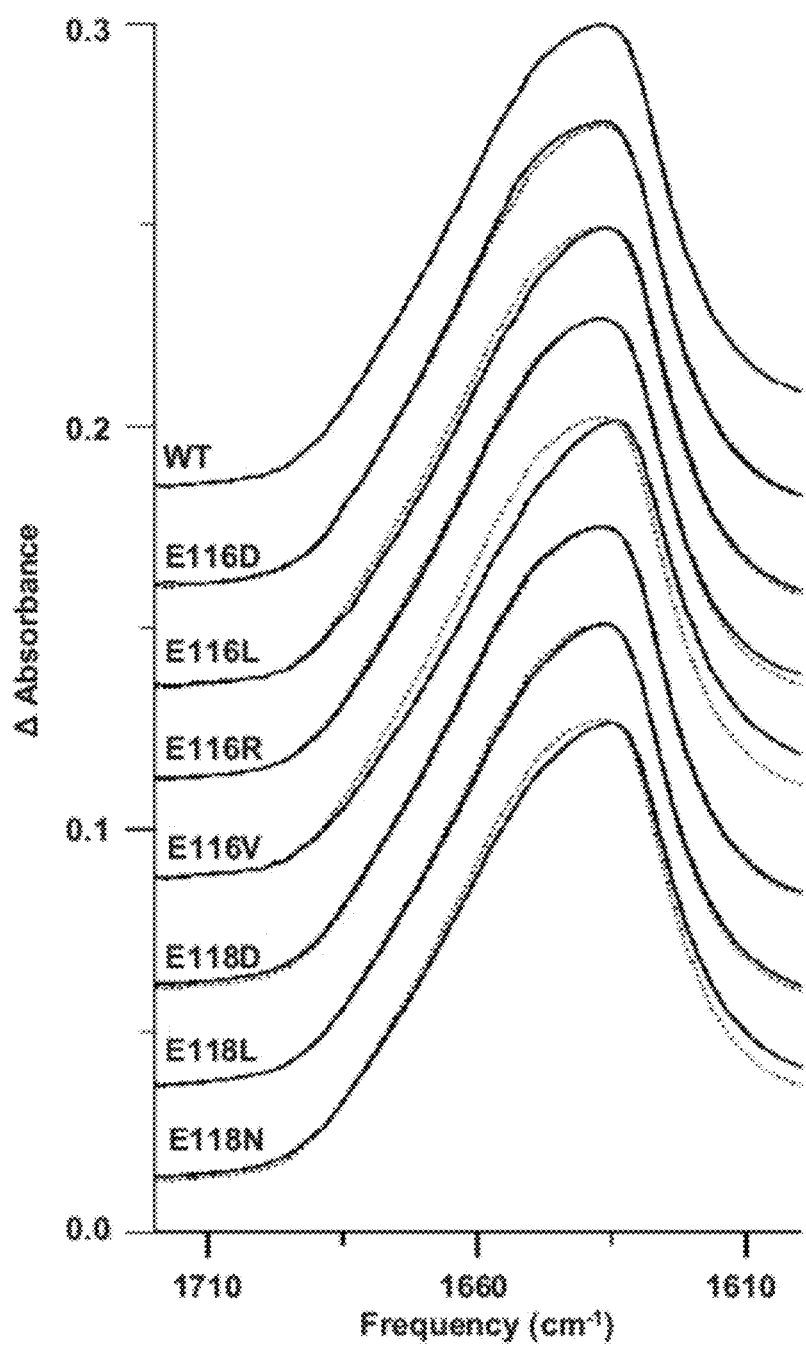
FIG. 4A illustrates plots of the averaged Fourier-transform infrared (FTIR) spectra of the amide I' region of wildtype, E116 mutant, and E118 mutant polymorphisms. The wildtype spectra are superimposed (dotted line) on each trace and differences in line shape are highlighted, showing quantitative changes in secondary structure. FTIR spectra were acquired from two independent purifications and averaged.
Figure 4B:
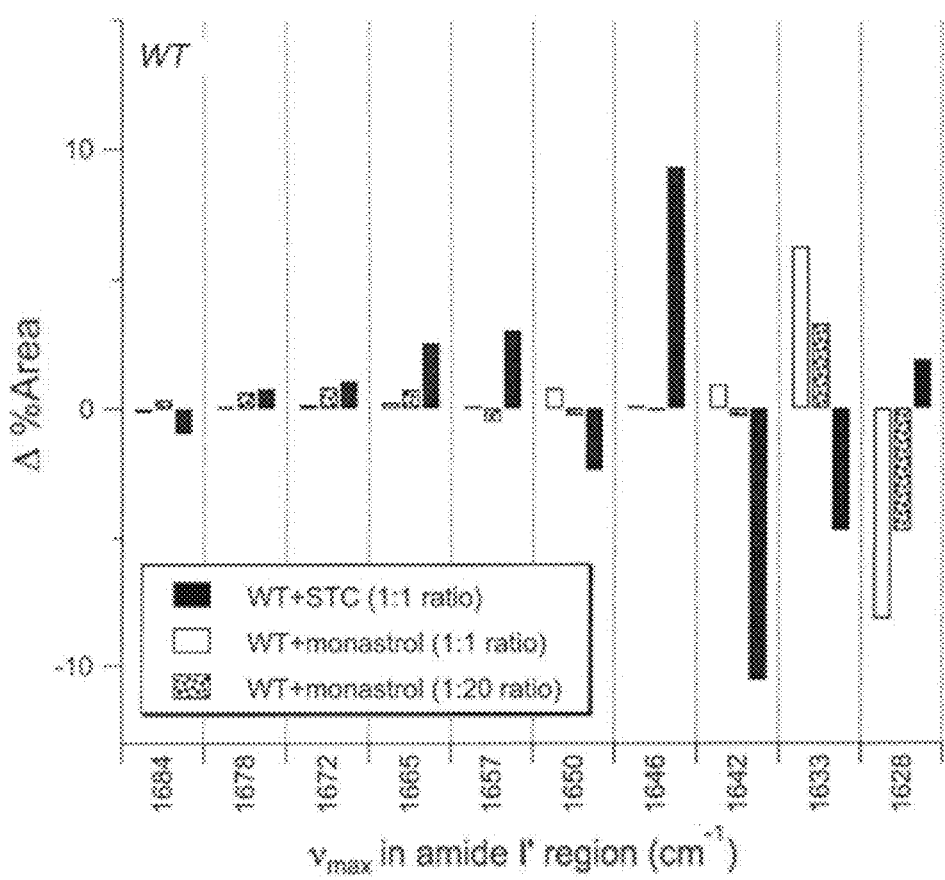
FIGS. 4B-D illustrate the results of band narrowing of the amide I' region of the N-terminal L5 residues into 10 frequency bins shown on the horizontal axis. Positive amplitudes indicate a gain of secondary structure at a given frequency from wildtype, while negative amplitudes indicate a loss of structure.
Figure 4C:
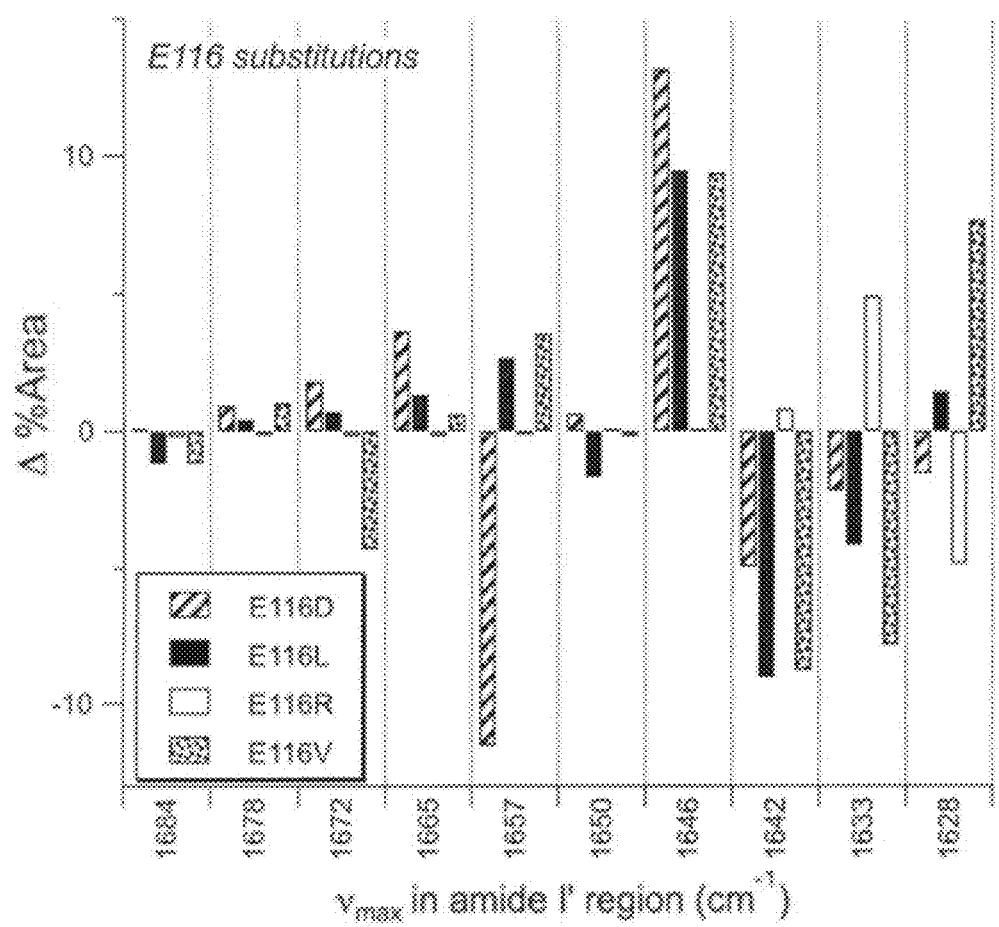
Figure 4D:
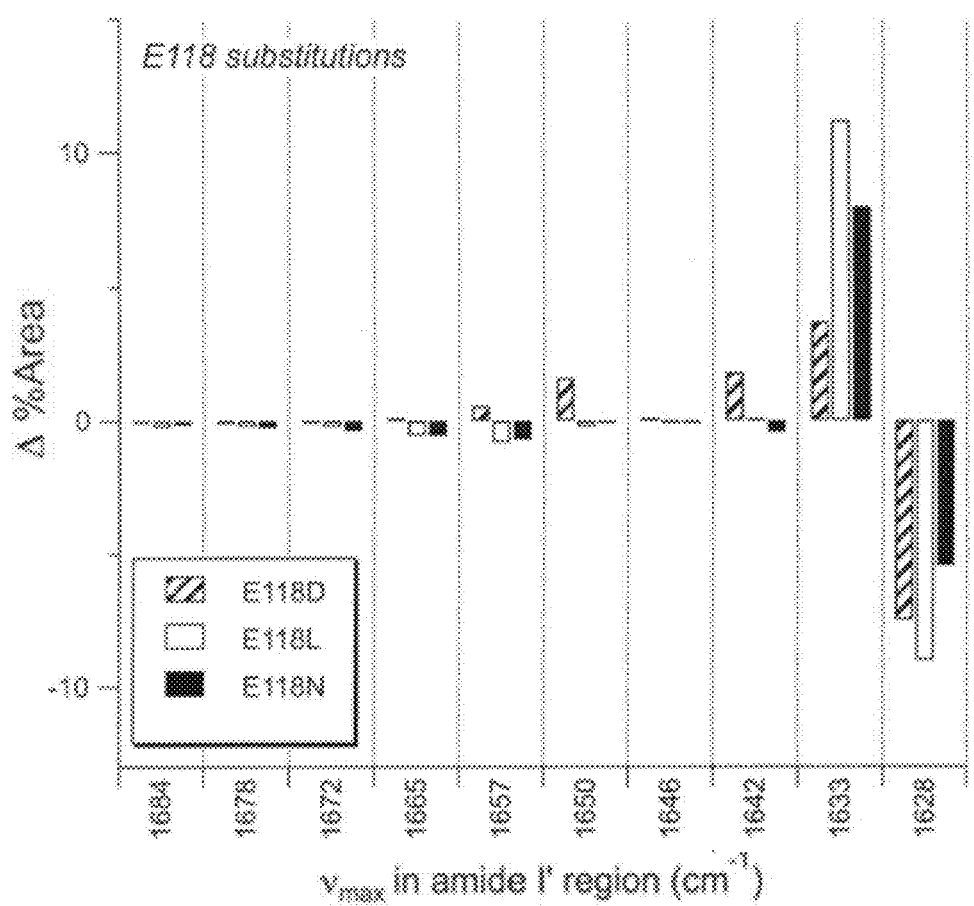

FTIR spectra were acquired on wildtype and all mutant Eg5 proteins alone and in the equimolar presence of monastrol or STC. Shown in FIG. 4A is a subset of the averaged spectral data on $^2H_2O$-exchanged Eg5 proteins in the amide I' region (1720-1600 $cm^{-1}$). The normalized data share broadly similar lineshapes, arguing for similar overall secondary structure composition. Secondary structure contributions can be accurately measured through band narrowing and regression analysis (38,39) on averaged FTIR spectra (FIG. 3A-3C). Differences in amplitude for each frequency component measure proportionate changes in net secondary structure motifs between wildtype and mutant proteins. These quantitative changes are revealed after digital subtraction of the parent spectra, and can be decisively assigned to the gain or loss of structural motifs (FIG. 4B).

FTIR spectra on wildtype Eg5 proteins in the presence of allosteric inhibitors record structural changes that occur as a result of perturbing the L5 loop. Eg5·monastrol samples (FIG. 4B, top panel) have a 6% increased content for the 1633 $cm^{-1}$ spectral component and a 8% decreased content for the 1628 $cm^{-1}$ constituent, in comparison to uninhibited wildtype. From correlations of amide I' band frequency with secondary structural elements in proteins in $^2H_2O$ (40,41), both the 1628 $cm^{-1}$ and 1633 $cm^{-1}$ are assigned to low-frequency component of β-sheets. These changes are well above the level of noise: variation from wildtype to wildtype sample was typically less than 1% at a given frequency (data not shown).

In contrast, the major changes between wildtype Eg5·STC and ligand-free wildtype samples are measured for the 1646 $cm^{-1}$ and 1642 $cm^{-1}$ spectral components, attributable to 9% increase in disordered structure and 10% decrease in $3_{10}$ helical content, respectively. Thus, interaction of wildtype Kinesin-5 protein with monastrol results in different spectral amide I' components than STC binding. Changes in the high-frequency beta sheet components at 1684, 1678, and 1672 $cm^{-1}$ were minimal in both wildtype Eg5·STC and Eg5·monastrol bound samples. The 1665, 1657, and 1650 $cm^{-1}$ modes, assignable to turns and alpha helices, show alterations in these structural elements between Eg5 bound with STC and bound with monastrol.

Alterations in peak height and shape of the broad amide I' envelope are detected also in the mutant Eg5 proteins (FIG. 4A). Difference spectra comparing mutant and wildtype data were obtained in a similar fashion to those described above, digitally subtracted and shown in FIG. 4B, middle and bottom panels. In general, E116 mutants have largest absorbance changes at 1646, 1642, 1633, and 1628 $cm^{-1}$ and they show similar vibrational markers to STC-inhibited wildtype samples. (FIG. 4B, middle panel) E118 mutants have the largest changes in area at 1633 and 1628 $cm^{-1}$ and they show similar vibrational markers to monastrol-inhibited wildtype samples. (FIG. 4B, bottom panel) As the overall pattern of secondary structural changes falls into either STC-like or monastrol-like spectrotypes, these data suggest two different populations of Eg5 conformers for these N-terminal L5 mutations. This interpretation is supported by the anomalous gel migration in FIGS. 1A-1D. Thus, the N-terminal L5 substitutions result in modular changes in secondary structure of Eg5 in solution, irrespective of mutation or drug-binding.

Figure 5A:
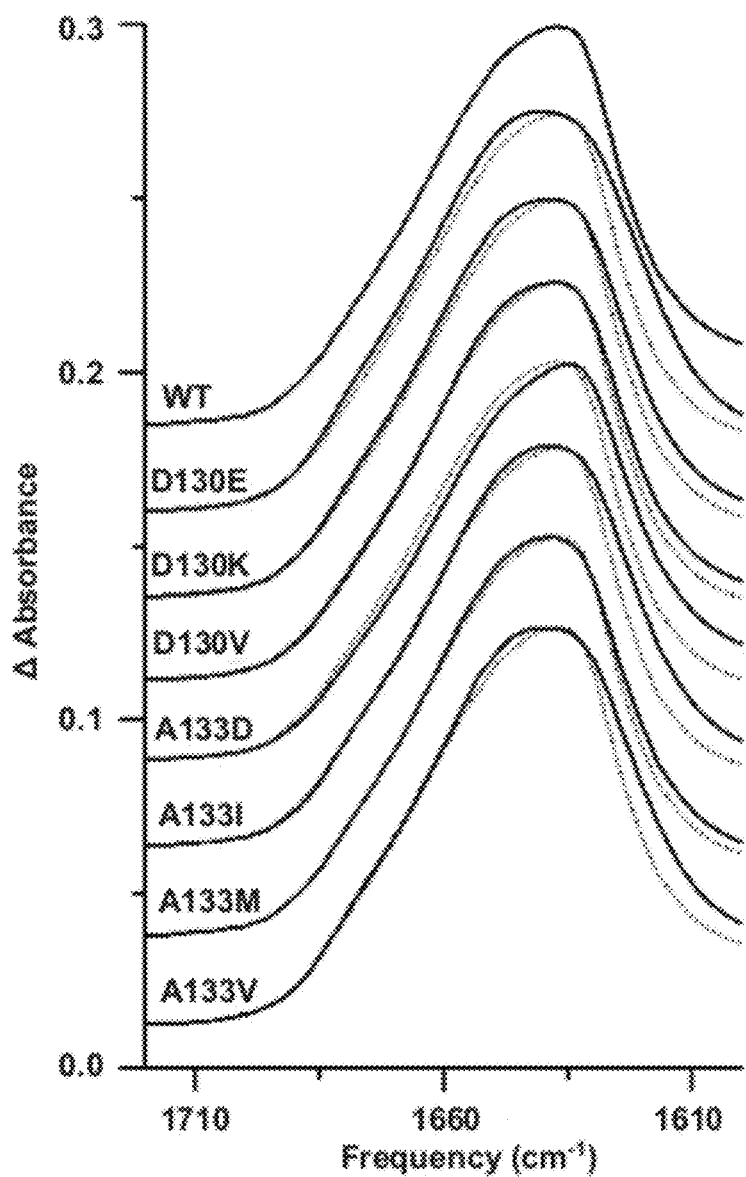
FIG. 5A illustrates plots of the averaged Fourier-transform infrared (FTIR) spectra of the amide I' region of wildtype, D130 mutant, and A133 mutant polymorphisms. The wildtype spectra are superimposed (dotted line) on each trace and differences in line shape are highlighted, showing quantitative changes in secondary structure. FTIR spectra were acquired from two independent purifications and averaged.
Figure 5B:
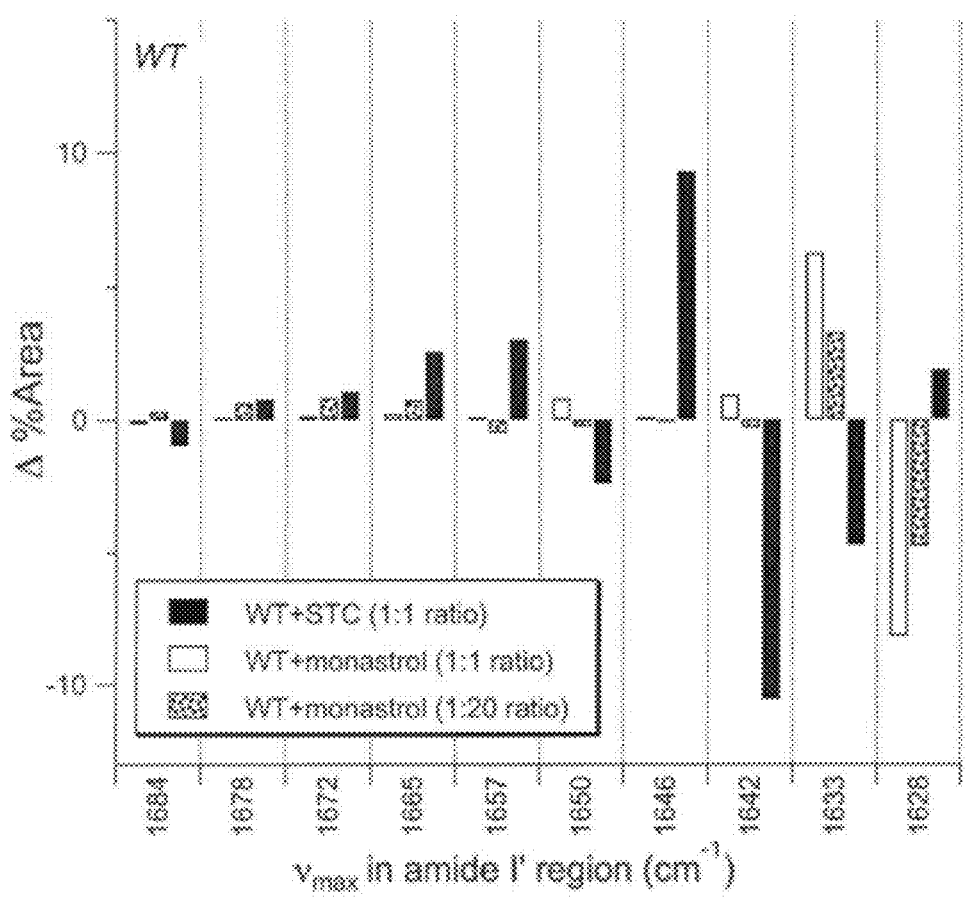
FIGS. 5B-D illustrate the results of band narrowing of the amide I' region of the N-terminal L5 residues into 10 frequency bins shown on the horizontal axis. Positive amplitudes indicate a gain of secondary structure at a given frequency from wildtype, while negative amplitudes indicate a loss of structure.
Figure 5C:
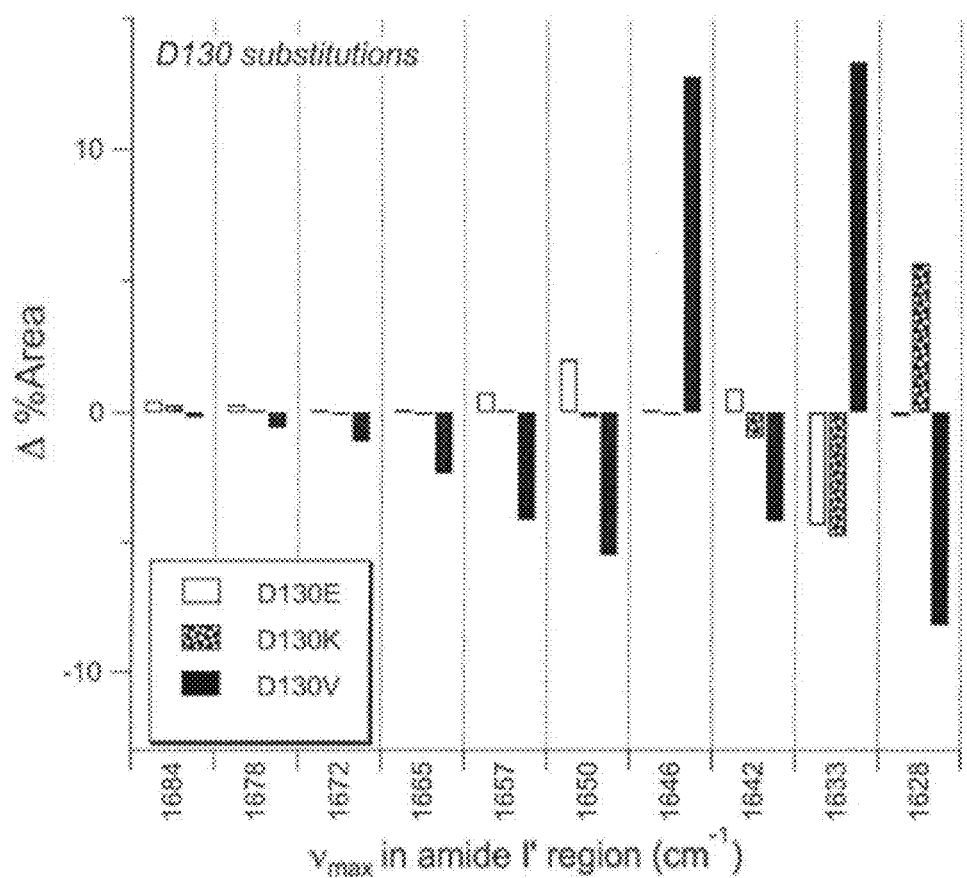
Figure 5D:
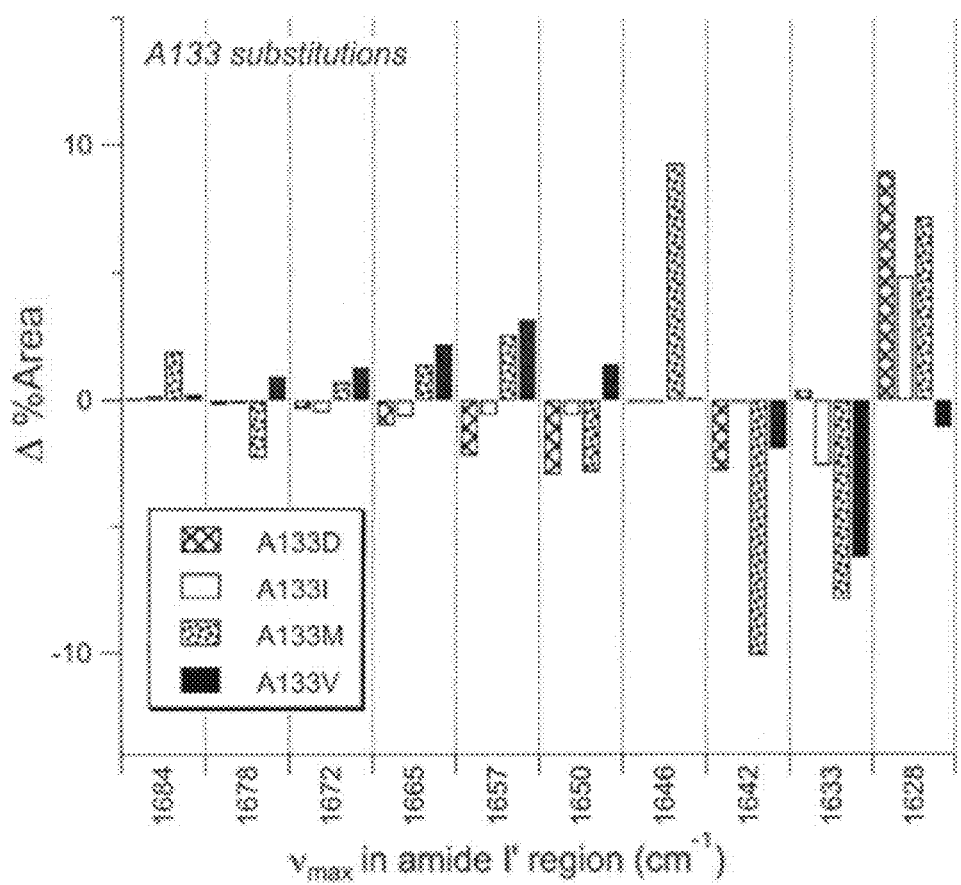

Similar analyses were conducted for IR spectra collected from C-terminal L5 mutants in solution, in both their free- and ligand-bound forms. Substitution of A133 or D130 resulted in a greater number of possible conformational outcomes, as observed in the vibrational data (FIGS. 5A and 5B). Overall, there was not a clear catalogue of conformational changes in the C-terminal L5 mutants, compared to the N-terminal L5 mutants. The C-terminal L5 mutants had the largest absorbance changes at 1646, 1642, 1633, and 1628 $cm^{-1}$ and additional absorbance changes at 1665 and 1657 $cm^{-1}$ (FIG. 5A). Some of these C-terminal A130 and D133 substitutions exhibited similar changes in secondary structural content to the E116 mutants (FIG. 4B compared to FIG. 5B). However, other mutants in the C-terminus of the L5 loop had perturbations that are unique. Thus, as the C-terminal L5 mutants did not fall uniformly into the same spectrotype as STC- or monastrol-bound samples, these results suggested the long-range conformational effects are dependent on the chemical nature of the of the C-terminal residue sidechain.

Example 5

Exploratory Principal Component Analysis Identifies that N-Terminal L5 Mutants Occupy a Bimodal Structural Distribution in Solution To create a model of how Eg5 undergoes allosteric conformational changes propagated from the L5 loop, a computationally-driven multivariate data analysis was used to extract structural information from the IR data. Techniques for deconvoluting multivariate data are common analytic tools in microarray data, systems biology studies, and chemometric detection (42-46), but its implementation for discovering atomic-level information is novel. The vibrational spectrum is fundamentally multivariate and complex in nature. Within a series of discrete measurements at defined frequency intervals found in each spectrum, the vast number of normal modes in the Kinesin-5 motor domain (>15,000 vibrational degrees of freedom) can have frequency overlap.

The initial foray into multivariate data analysis used principal component analysis (PCA). This non-parametric method that uses eigenvectors was applied to decompose vibrational spectra to a smaller set of computer-derived variables and to form models for predicting factors causing responses. Although PCA does not directly relate cause and effect, it serves to highlight the larger variations in the input data and find patterns in a set of spectra that on the surface can appear similar. Lastly, use of statistical algorithms to categorize the FTIR data provided an unbiased method that is mathematically grounded.

Spectroscopic data from the N-terminal and C-terminal L5 mutants were subjected to exploratory PCA. For proper formation of an initial model and for proper evaluation of the model prediction, cross-validation methods were not used, but rather the data was partitioned into two spectral data sets to be evaluated independently. By not using a sample before testing it, any bias was eliminated in the prediction accuracy (47). Wildtype Eg5 and the N-terminal L5 mutants served as the training set for PCA. The query, or test, set was the C-terminal L5 mutant spectra, used to verify and refine the predictive model. This evaluation step, which included analysis of a second purified wildtype sample, was physically and temporally distinct from development of the initial training set.

The spectroscopic inputs are the band-narrowed amide I' frequencies from Eg5 protein in the absence of inhibitor, in the presence of monastrol, and in the presence of STC. In the outputs from these multivariate analyses (FIGS. 6A-6C), the principal components (PC1 and PC2), or variables of the projection space, are linear combinations of the original frequencies.

Using wildtype and N-terminal L5 mutant Kinesin-5 proteins, distinct patterns were obtained from PCA. Of the ten-dimensional PCA output of IR frequencies projected on a two-dimensional plane formed by PC1 and PC2, four dominant vectors, defined by the 1642, 1646, 1633 and 1628 cm$^{-1}$ IR frequencies, were found that accounted for 85% of the variance in the spectra in FIG. 6A. These patterns defined the amide I' frequencies associated with the E118 and E116 mutations and separated the motor proteins into two populations of conformers with high correlation. The first group contained E118 mutants and wildtype Eg5 (filled circles) in a tightly-clustered population. The second group was predominantly comprised of E116 mutants and the E116D-E118D double mutant (filled diamonds).

The 1642 and 1646 cm$^{-1}$ vectors (dotted rays, FIG. 6A) were the most influential in distinguishing the two mutant populations. This principal component analysis emphasized the strong connection between residue substitution in the N-terminus of the L5 loop and changes in $3_{10}$ helical content and disordered structures, respectively. The 1633 and 1628 cm$^{-1}$ vectors (FIG. 6A) also discriminated between the mutant populations, linking changes in Eg5 β-sheets with perturbations of the L5 loop.

The results from PCA were further supported by examination of additional protein samples that were not used in the initial model-building step. Independent PCA analysis of the C-terminal L5 mutants (FIG. 6B) also accounted for approximately 85% of the variance in these spectra. PCA of these test FTIR spectra (FIG. 6B) place the D130 and A133 mutants within identical structural populations of the N-terminal L5 mutants and predominantly fall into line with the wildtype/E118 data points. The fidelity of the training and test sets for this PCA experiment supports the conclusion that the initial model accurately predicted the conformer populations of Eg5 motor domains in which the L5 loop is challenged. Additionally, the high PCA correlation supports the conclusion that the curation of Eg5 structures sampled a sufficient number of conformational possibilities to inform reasonable allosteric models.

In summary, spectroscopic signatures exhibited by drug-resistant variants were similar to those of wildtype human Eg5 (or KSP) inhibited by small-molecules. The above Eg5 variants are resistant to inhibition because their solution structure has already poised in the 'inhibited' state that may catalytically block the transition state. These convergent steady-state changes to the secondary structure of the Eg5 motor domain also supports the conclusion that the spectroscopic signature can serve as a biomarker for determining resistance to targeted chemotherapeutics in patient treatment. Thus, high-throughput measurement of modular conformation secondary structural changes within the human Eg5 motor domain permits conformational profiling of drug-resistant proteins.

Example 6

Monastrol and STC Produce Similar Local, but Dissimilar Distal, Structural Changes Statistical algorithms were applied to infrared data to reveal features that were the basis for discriminating between the effects of monastrol and STC. The presence of monastrol or STC resulted in coincident, steady-state structural changes in mutant kinesin proteins (FIG. 6C): protein-inhibitor samples were separated by the 1646 and 1642 cm$^{-1}$ components and fell into the same two PCA populations as free protein. This supports the conclusion that analogous modifications in disordered and $3_{10}$ helical content are reproducibly created in both Eg5 mutants and in allosteric inhibition.

Figure 6A:
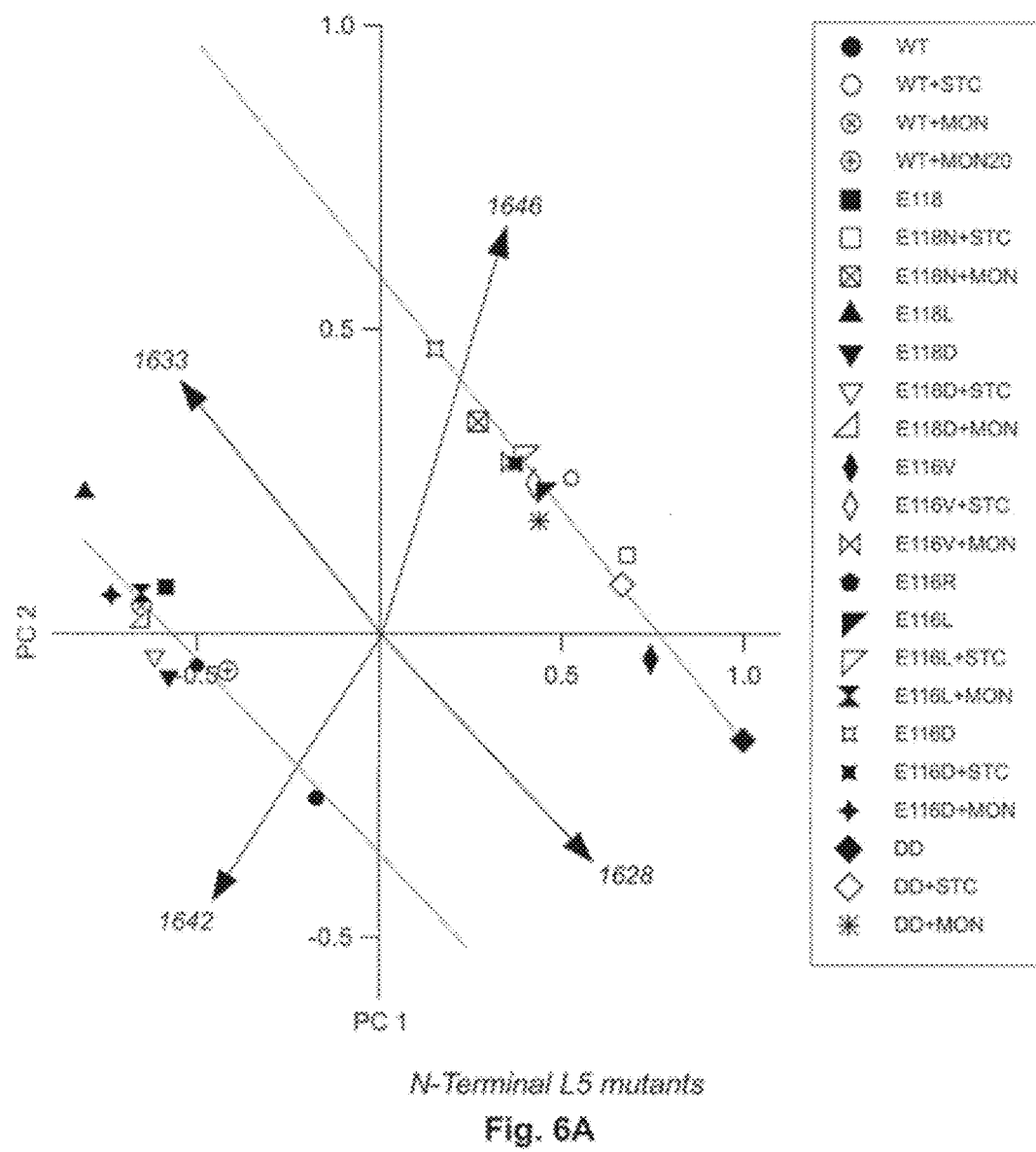
FIG. 6A illustrates the results of PCA analysis for the E116 and E118 mutant proteins, the N-Terminal L5 mutants. The score, or spatial positioning, of the data points is based on changes in percent area of the secondary structure profiles determined by band narrowing. PCA clustered the majority of E118 (■) and WT (●) data points based on secondary structure. The E116 (□) polymorphisms fell into a separate line of degeneracy with a larger disordered component. The 1642 and 1646 cm$^{-1}$ vectors separate these two populations.
Figure 6B:
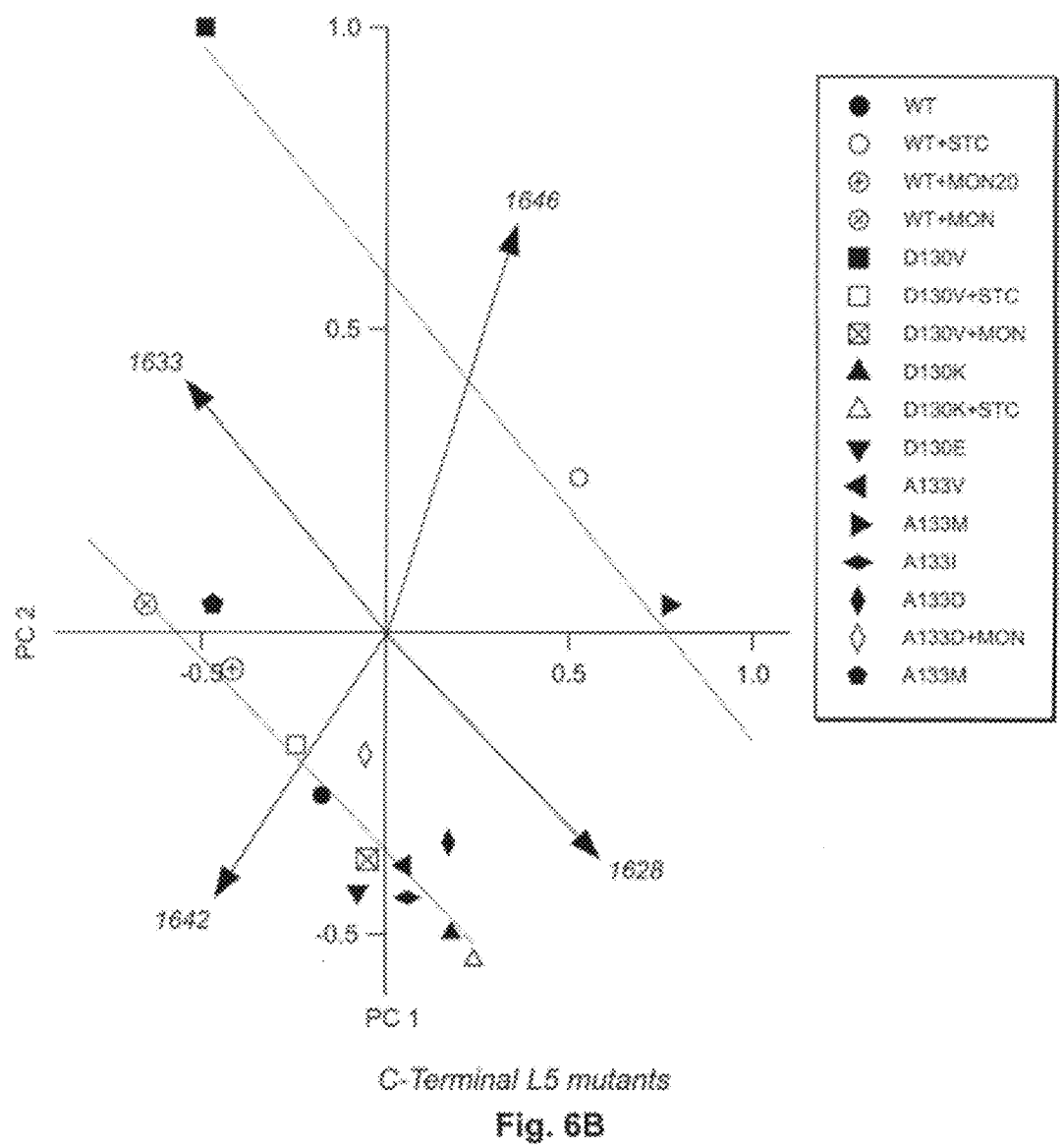
FIG. 6B illustrates the results of PCA analysis for the D130 and A133 mutant proteins, the C-Terminal L5 mutants. The score, or spatial positioning, of the data points is based on changes in percent area of the secondary structure profiles determined by band narrowing. PCA of C-terminal L5 residues, A133 (▲) and D130 (Δ), fell predominantly into the same population occupied by the N-terminal E118 mutations and can be differentiated by the 1633 and 1628 cm$^{-1}$ vectors, respectively.
Figure 6C:
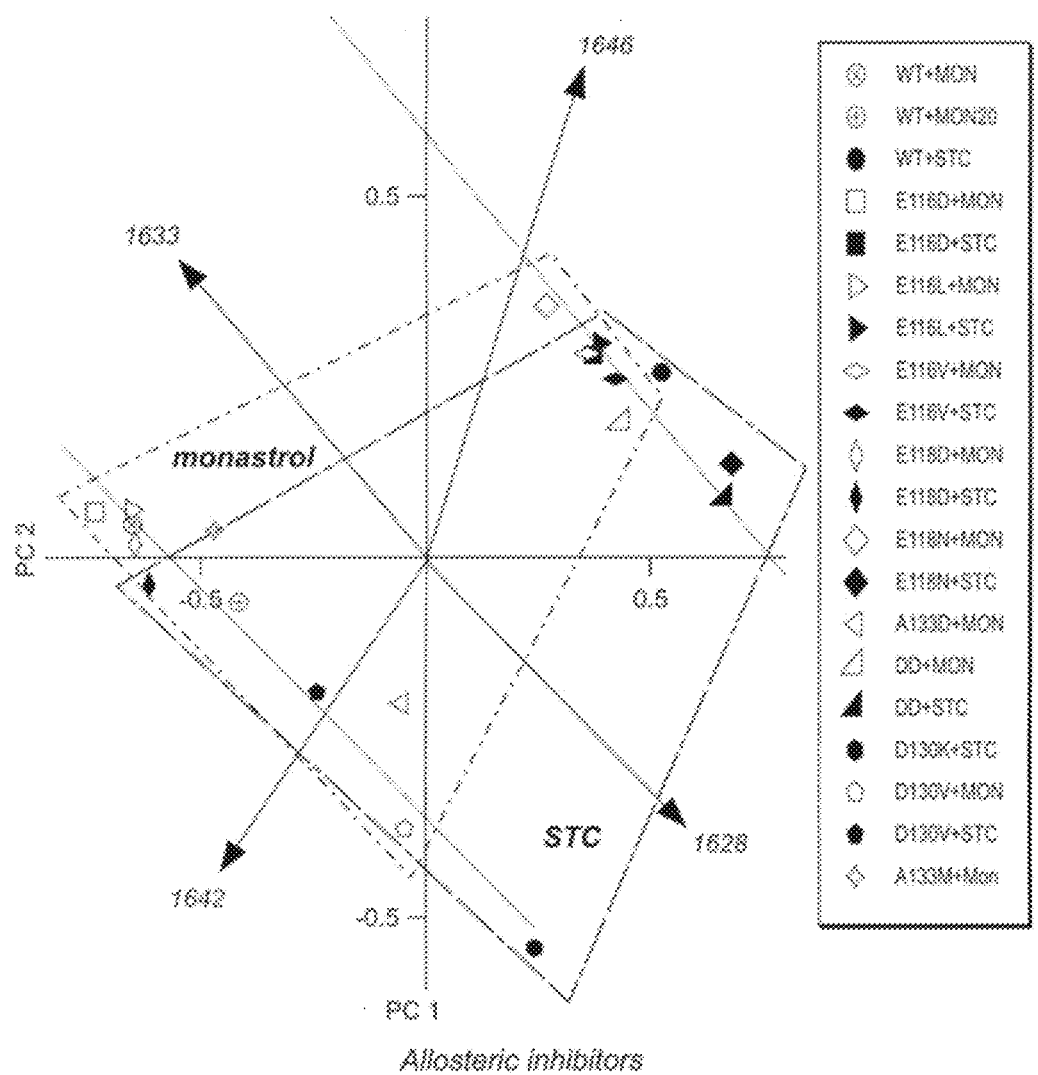
FIG. 6C illustrates the results of PCA analysis for a composite of both N- and C-terminal polymorphisms. Highlighted are the monastrol and STC data points.

The 1633 and 1628 cm$^{-1}$ components differentiated the clustering of Eg5 samples incubated with monastrol or with STC (FIG. 6C). Regardless of which population the data points fell into, STC samples of the parent mutant generally had a greater 1628 cm$^{-1}$ component (FIG. 6C, short dashed box), whereas monastrol samples had a greater 1633 cm$^{-1}$ component (FIG. 6C, long dashed box). The 1633 and 1628 cm$^{-1}$ frequencies arose from changes in β-sheet structures, which are found at the core of all kinesin motor domains. This PCA analysis underscored that, by IR spectroscopy, long-distance changes to β-sheets within the kinesin protein have been measured, changes that are a requirement for allostery. Moreover, the 5 cm$^{-1}$ difference between the β-sheet components indicated that each frequency arose from a unique perturbation of this secondary structure. Thus, more than one means exist by which L5-initiated perturbations are coupled to distant secondary elements.

These observations by vibrational methods were corroborated by comparison of crystal structures of wildtype Eg5·ADP bound with monastrol (17) or STC. The 2.5 Å X-ray crystallographic determination of Eg5·ADP bound with a single STC molecule (Table 2) showed a canonical arrowhead-shaped globular structure. STC and monastrol were observed to stabilize similar overall states of the motor domain. The necklinker is positioned in the "docked" conformation seen in the monastrol-bound Eg5 structures, and the switch I and II regions also adopt conformations similar to those observed for bound monastrol.

TABLE 2

| X-ray refinement statistics | |
|---|---|
| Resolution (Å) | 2.5 |
| $R_{work}/R_{free}$ | 0.241/0.275 |
| Number of atoms | 2749 |
| Protein | 2617 |
| Ligand/ion | 58 |
| Water | 74 |
| B-factors | |
| Protein | 25.537 |
| Ligand/ion | 26.120 |
| Water | 18.767 |
| R.M.S deviations | |
| Bond lengths (Å) | 0.008 |
| Bond angles (°) | 1.426 |

As expected from other crystallographic studies of Eg5 inhibitors, there were no large differences in the local structure of the allosteric site in the Eg5·ADP·STC structure. The overall fold of the L5 loop was similar to that of two published monastrol-bound Eg5 structures. However, STC binding resulted in a slightly greater restriction of the allosteric site by the L5 loop: STC binding occludes approximately 80 Å$^2$ more of the Eg5 surface from solvent access than does monastrol. Of the residues examined in this study, only the rotamer configuration of E118 in Eg5·ADP·STC differed slightly from monastrol-bound Eg5.

Long-range structural effects were shown in the β-sheet core of the motor domain, due to binding of L5-directed inhibitors. The central β-sheet structure of all kinesin motor domains consists of a parallel β-sheet, with a topology (or (3-strand order) of 2183, adjacent to an antiparallel β-sheet with a topology of 7645. There are clear distortions of the antiparallel β-sheet that likely impose novel strain on the motor domain core in presence of these allosteric inhibitors.

Strands that undergo the largest changes are β4, β5, β6, and β7. Although all strands typically exhibit a right-handed twist in higher-order structures, the N-terminus of the β4 strand is pulled closer to the α2 helix in both STC- and monastrol-bound structures, compared to the native Eg5 structure. The β5 strand is not formed in the Eg5·STC structure. The (36 and 137 strands have large distortions that differ in magnitude and direction, dependent on whether STC or monastrol was bound to the L5 loop. Direct comparison of the STC- and monastrol-bound Eg5 structures stresses the divergence in the twist of the β6 and β7 strands. Exaggeration in the twist of the β6 and β7 strands are also observed in other structures of Eg5 co-crystallized with L5-directed inhibitors.

Example 7

A High Prediction Accuracy Exists Between IR and X-Ray Diffraction Determination of Eg5 Helical Structures Current IR data did not inherently contain information on the precise site(s) of origin within the Eg5 motor domain. Inspection of relevant crystal structures can facilitate the further assignment of an IR signature to a specific protein segment. Examination of fractional secondary structure content of wildtype Eg5 motor proteins determined from X-ray diffraction methods supported the multivariate findings of Kinesin-5 in solution. From DSSP analysis (48) of Eg5 structures in the PDB, increased $3_{10}$ helix content was observed when comparing ligand-bound versus free Eg5 proteins (Table 3). In Eg5·ADP crystal structures (22), four $3_{10}$ helices were found within the α3, α5, and α6 helices and in the switch I loop. Thus, 3.3% of residues in the Eg5 motor domain were found in $3_{10}$ helices in Eg5·ADP crystal structures. In inhibitor-complexed Eg5 proteins, there was generally a gain of two $3_{10}$ helices in the L5 loop, increasing the fractional content of $3_{10}$ helices to 4.9%

TABLE 3

Comparison of fractional secondary structure composition in inhibitor-free and inhibitor-bound crystal structures of Eg5.

| | % change in secondary structure | | | | | |
|---|---|---|---|---|---|---|
| Compared structures | β-sheet | α-helix | $3_{10}$ helix | turn | bend | β-bridge |
| 3KEN - 1II6 (STC) | −0.7 | 1.5 | 0.0 | −1.5 | 0.8 | 0.0 |
| 1Q0B - 1II6 (mon) | 3.0 | −1.4 | 1.6 | 0.3 | −0.7 | 0.0 |
| 1X88 - 1II6 (mon) | 2.3 | −1.5 | 1.6 | 0.9 | −1.6 | 0.0 |
| 1YRS - 1II6 | 0.0 | −2.4 | 1.2 | 1.2 | 0.9 | −0.3 |
| 2IEH - 1II6 | 2.7 | −2.6 | 0.0 | 2.4 | 0.7 | −0.3 |

Secondary structure assignments in crystallographic data are obtained from DSSP analysis. Fractional compositions were calculated for each protein within the asymmetric unit cell and averaged, when appropriate.
Subtraction of inhibitor-bound values from inhibitor-free Eg5 structures is shown.

Although the IR spectrum is a reflection of the motor protein ensemble, it is believed that the above IR-detectable changes at 1642 and 1646 cm$^{-1}$ are localized to the L5 loop, as it is the only protein segment that shows a conformational isomerization between $3_{10}$ helices and a random loop. Moreover, this stringent comparison between the solution structural determinations and crystallographic data calls attention to the sensitivity of the vibrational methods employed here: even changes in 6 residues can be accurately detected within the amide I' envelope.

Example 8

These IR Spectrotypes Serve as Novel Structural Biomarkers to Predict Drug Sensitivity The above experiments demonstrate that inhibitor efficacy can be measured structurally: it is predicted that a large 1628 cm$^{-1}$ component would be observed in PCA of more potent inhibitors of Eg5. The uncovered interactions that are essential in determining drug sensitivity in Eg5 mutants in vitro can be extended to predicting how human polymorphisms can affect clinical responsiveness.

Herein particular structural signatures were demonstrated to be correlated with inhibitor resistance in Eg5 variants. The first condition for inhibitor resistance in Eg5 is the conformational selection of the L5 loop in solution. For the N-terminal L5 substitutions, there was a clear difference in the pattern of secondary structure changes observed in the E116 mutant proteins when compared to those of the E118 substitutions (FIGS. 4A, 4B, and 6A). The kinetic sensitivity of E118 mutants to drug inhibition (FIGS. 2A and 2E) is correlated with adoption of $3_{10}$ helical structure in the L5 loop and a large 1642 cm$^{-1}$ vector (FIG. 6A). In line with this conclusion, the clustering of the E116 mutant samples in PCA indicated that a large 1646 cm$^{-1}$ component was strongly correlated with drug resistance. Thus, loss of the $3_{10}$ helix in the L5 loop unilaterally prohibits binding of small molecules to the allosteric site, as shown by the D130V mutation that confers resistance in Eg5 to the clinical trial drugs in purified form, in tumor cell culture, and in xenograft model systems (32,33).

Another component in inhibitor resistance in Kinesin-5 proteins is the mechanochemical state of the antiparallel β-sheet. For Eg5 variants that populate the 1646 cm$^{-1}$ cluster in the principal component analysis, the lack of $3_{10}$ helix functionally overrides any conformational changes observed in the β-sheet. Therefore, there is a hierarchy of structural changes that dictate inhibitor resistance. For Eg5 variants that populate the 1642 cm$^{-1}$ cluster in PCA, only genotypes that result in strong 1633 cm$^{-1}$ vectors remain sensitive to drug inhibition. If there is a twist of the β6 and β7 strands that resembles the STC-bound Eg5 and thus exhibits a strong 1628 cm$^{-1}$ component in multivariate analysis (FIG. 6B), this torque on the antiparallel β-sheet negates drug sensitivity, even if $3_{10}$ helices are adopted. This is the case for the established ispinesib-resistant mutant, A133D.

From this work, it is believed that isomerization of the L5 loop and distortions of the central β-sheet can also serve as novel structural biomarkers to predict drug sensitivity of Eg5. This biomarker provides correlation between protein structure and therapeutic outcome, which is advantageous because the final target for clinical drugs is typically polypeptides. Case in point, more than half of the mutants examined had catalytic rates comparable or greater than wildtype samples. Seemingly normal Eg5 kinesin function could harbor a polymorphism that would confer resistance to clinical drugs, and this biomarker could discriminate against Eg5-directed inhibitors. This is a rapid and quantitative method for assaying conformational alterations, resulting from peptide sequence variations, of protein ensembles in solution. This biophysical approach answers 'how much' an individual protein variant is resistant to a drug. It is believed that these structural biomarkers based on conformational changes due to the sequence polymorphism can be used in the clinic for appropriate treatment options for kinesin-related diseases.

Quantitative measurement of structural changes as a function of inhibitor concentration will provide preliminary data toward establishing correlations between the relative amount of structural changes invoked by a polymorphism and the concentration of a compound necessary to inhibit the variant protein.

It is believed that the use of structural biomarkers is extendable to other protein targets for cancer drugs. The tyrosine kinase, BCR-ABL, will be tested with these methods, as it has the greatest molecular, biochemical, and structural information available and there are two generations of inhibitors in current clinical use. The BCR-ABL oncogene, which is the product of the Philadelphia chromosome 22q, encodes a chimeric BCR-ABL protein that has constitutively activated ABL tyrosine kinase activity and is the underlying cause of chronic myeloid leukemia (CML). The impact of Gleevec, a small molecule inhibitor of the oncogenic form of this protein, on the field of cancer therapy has been dramatic. This drug is the current gold standard of targeted chemotherapy, as it has not only changed how newly diagnosed patients with CML are treated, but it also improves their prognosis. Gleevec resistance can develop in patients, typically caused by point mutations to the kinase domain that reduce binding of Gleevec by either direct or indirect mechanisms. This structural biomarker can be applied to purified proteins from patient samples. This method can be used to locate a structural biomarker for BCR-ABL and offer new information on mutants that ablate Gleevec binding by indirect mechanisms and for which no reason for resistance has been established.

Lastly, the finding and describing of fully-developed structural biomarkers can predict drug efficacy in patients. Future treatment strategies will be based on an analysis of an individual's cancer cells or other cells, and proteins from those cancer cells or other cells, which would then allow development of a profile of likely sensitivity of the proteins to targeted therapies. Based on this information, each individual might then be assigned to a combination regimen that best matches the profile from the cancer cells or other cells. Toward this treatment strategy, initial efforts will examine documented medication response profiles and somatic polymorphisms of patients in the National Cancer Institute's Surveillance, Epidemiology, and End Results (SEER) Program. The SEER registries routinely collect data on patient demographics, primary tumor site, tumor morphology and stage at diagnosis, first course of treatment, and outcome data (survival). In addition, the Residual Tissue Repository (RTR) program provides representative sampling of biospecimens associated with SEER patients for testing. Somatic polymorphisms can be determined for patients who were treated with tyrosine kinase inhibitors. When kinesin spindle protein (KSP) inhibitors are adopted into standard clinical practice, parallel experiments can be performed as well.

Clinical trials will evaluate whether oncologists use of structural biomarkers improves therapeutic response in patients. In the process of achieving a more individualized treatment strategy, this clinical trial will evaluate the performance of 'random' selection of agents (current practice), genomic signature-based selection, structural biomarker selection, or a combination of genomic- and spectroscopic signatures for selection. This would evaluate the predictive value of the different types of biomarkers toward therapeutic response in the hands on physicians.

REFERENCES

1. Gunasekaran, K., Ma, B., and Nussinov, R. (2004) *Proteins* 57, 433-443
2. Monod, J., Wyman, J., and Changeux, J. P. (1965) *Journal of molecular biology* 12, 88-118
3. Kern, D., and Zuiderweg, E. R. (2003) *Current opinion in structural biology* 13, 748-757
4. Cooper, A., and Dryden, D. T. (1984) *Eur Biophys J* 11, 103-109
5. Hotha, S., Yarrow, J. C., Yang, J. G., Garrett, S., Renduchintala, K. V., Mayer, T. U., and Kapoor, T. M. (2003) *Angewandte Chemie (International ed* 42, 2379-2382
6. DeBonis, S., Skoufias, D. A., Lebeau, L., Lopez, R., Robin, G., Margolis, R. L., Wade, R. H., and Kozielski, F. (2004) *Mol Cancer Ther* 3, 1079-1090
7. Sunder-Plassmann, N., Sarli, V., Gartner, M., Utz, M., Seiler, J., Huemmer, S., Mayer, T. U., Surrey, T., and Giannis, A. (2005) *Bioorg Med Chem* 13, 6094-6111
8. Maliga, Z., Kapoor, T. M., and Mitchison, T. J. (2002) *Chemistry & biology* 9, 989-996
9. DeBonis, S., Simorre, J. P., Crevel, I., Lebeau, L., Skoufias, D. A., Blangy, A., Ebel, C., Gans, P., Cross, R., Hackney, D. D., Wade, R. H., and Kozielski, F. (2003) *Biochemistry* 42, 338-349
10. Mayer, T. U., Kapoor, T. M., Haggarty, S. J., King, R. W., Schreiber, S. L., and Mitchison, T. J. (1999) *Science* 286, 971-974
11. Brier, S., Lemaire, D., Debonis, S., Forest, E., and Kozielski, F. (2004) *Biochemistry* 43, 13072-13082
12. Cox, C. D., Breslin, M. J., Mariano, B. J., Coleman, P. J., Buser, C. A., Walsh, E. S., Hamilton, K., Huber, H. E., Kohl, N. E., Torrent, M., Yan, Y., Kuo, L. C., and Hartman, G. D. (2005) *Bioorg Med Chem Lett* 15, 2041-2045
13. Cochran, J. C., Gatial, J. E., 3rd, Kapoor, T. M., and Gilbert, S. P. (2005) *The Journal of biological chemistry* 280, 12658-12667
14. Skoufias, D. A., DeBonis, S., Saoudi, Y., Lebeau, L., Crevel, I., Cross, R., Wade, R. H., Hackney, D., and Kozielski, F. (2006) *The Journal of biological chemistry* 281, 17559-17569
15. Lad, L., Luo, L., Carson, J. D., Wood, K. W., Hartman, J. J., Copeland, R. A., and Sakowicz, R. (2008) *Biochemistry* 47, 3576-3585
16. Luo, L., Parrish, C. A., Nevins, N., McNulty, D. E., Chaudhari, A. M., Carson, J. D., Sudakin, V., Shaw, A. N., Lehr, R., Zhao, H., Sweitzer, S., Lad, L., Wood, K. W., Sakowicz, R., Annan, R. S., Huang, P. S., Jackson, J. R., Dhanak, D., Copeland, R. A., and Auger, K. R. (2007) *Nat Chem Biol* 3, 722-726
17. Maliga, Z., and Mitchison, T. J. (2006) *BMC Chem Biol* 6, 2
18. Yan, Y., Sardana, V., Xu, B., Homnick, C., Halczenko, W., Buser, C. A., Schaber, M., Hartman, G. D., Huber, H. E., and Kuo, L. C. (2004) *Journal of molecular biology* 335, 547-554
19. Fraley, M. E., Garbaccio, R. M., Arrington, K. L., Hoffman, W. F., Tasber, E. S., Coleman, P. J., Buser, C. A., Walsh, E. S., Hamilton, K., Fernandes, C., Schaber, M. D., Lobell, R. B., Tao, W., South, V. J., Yan, Y., Kuo, L. C., Prueksaritanont, T., Shu, C., Torrent, M., Heimbrook, D. C., Kohl, N. E., Huber, H. E., and Hartman, G. D. (2006) *Bioorg Med Chem Lett* 16, 1775-1779
20. Garbaccio, R. M., Fraley, M. E., Tasber, E. S., Olson, C. M., Hoffman, W. F., Arrington, K. L., Torrent, M., Buser, C. A., Walsh, E. S., Hamilton, K., Schaber, M. D., Fernandes, C., Lobell, R. B., Tao, W., South, V. J., Yan, Y., Kuo, L. C., Prueksaritanont, T., Slaughter, D. E., Shu, C., Heimbrook, D. C., Kohl, N. E., Huber, H. E., and Hartman, G. D. (2006) *Bioorg Med Chem Lett* 16, 1780-1783

21. Kaan, H. Y., Ulaganathan, V., Hackney, D. D., and Kozielski, F. (2009) *Biochem J*
22. Turner, J., Anderson, R., Guo, J., Beraud, C., Fletterick, R., and Sakowicz, R. (2001) *The Journal of biological chemistry* 276, 25496-25502
23. Cochran, J. C., and Gilbert, S. P. (2005) *Biochemistry* 44, 16633-16648
24. Bodey, A. J., Kikkawa, M., and Moores, C. A. (2009) *Journal of molecular biology* 388, 218-224
25. Parke, C. L., Wojcik, E. J., Kim, S., and Worthylake, D. K. (2009) *The Journal of biological chemistry* 285, in press
26. Maliga, Z., Xing, J., Cheung, H., Juszczak, L. J., Friedman, J. M., and Rosenfeld, S. S. (2006) *The Journal of biological chemistry* 281, 7977-7982
27. Brier, S., Lemaire, D., DeBonis, S., Kozielski, F., and Forest, E. (2006) *Rapid Commun Mass Spectrom* 20, 456-462
28. Wojcik, E. J., Dalrymple, N. A., Alford, S. R., Walker, R. A., and Kim, S. (2004) *Biochemistry* 43, 9939-9949
29. Deavours, B. E., Reddy, A. S., and Walker, R. A. (1998) *Cell Motil Cytoskeleton* 40, 408-416
30. Learman, S. S., Kim, C. D., Stevens, N. S., Kim, S., Wojcik, E. J., and Walker, R. A. (2009) *Biochemistry* 48, 1754-1762
31. Jones, T. A., Zou, J. Y., Cowan, S. W., and Kjeldgaard, M. (1991) *Acta Crystallogr A* 47 (Pt 2), 110-119
32. Blagden, S. P., Molife, L. R., Seebaran, A., Payne, M., Reid, A. H., Protheroe, A. S., Vasist, L. S., Williams, D. D., Bowen, C., Kathman, S. J., Hodge, J. P., Dar, M. M., de Bono, J. S., and Middleton, M. R. (2008) *Br J Cancer* 98, 894-899
33. Carol, H., Lock, R., Houghton, P. J., Morton, C. L., Kolb, E. A., Gorlick, R., Reynolds, C. P., Maris, J. M., Keir, S. T., Billups, C. A., and Smith, M. A. (2009) *Pediatr Blood Cancer* 53, 1255-1263
34. Garcia-Saez, 1., DeBonis, S., Lopez, R., Trucco, F., Rousseau, B., Thuery, P., and Kozielski, F. (2007) *The Journal of biological chemistry* 282, 9740-9747
35. Zhang, B., Liu, J. F., Xu, Y., and Ng, S. C. (2008) *Biochem Biophys Res Commun* 372, 565-570
36. Banci, L., Bertini, I., Cusack, S., de Jong, R. N., Heinemann, U., Jones, E. Y., Kozielski, F., Maskos, K., Messerschmidt, A., Owens, R., Perrakis, A., Poterszman, A., Schneider, G., Siebold, C., Silman, I., Sixma, T., Stewart-Jones, G., Sussman, J. L., Thierry, J. C., and Moras, D. (2006) *Acta Crystallogr D Biol Crystallogr* 62, 1208-1217
37. Barth, A., and Zscherp, C. (2002) *Q Rev Biophys* 35, 369-430
38. Goormaghtigh, E., De Meutter, J., Vanloo, B., Brasseur, R., Rosseneu, M., and Ruysschaert, J. M. (1989) *Biochimica et biophysica acta* 1006, 147-150
39. Hutchison, R. S., Betts, S. D., Yocum, C. F., and Barry, B. A. (1998) *Biochemistry* 37, 5643-5653
40. Susi, H., and Byler, D. M. (1986) *Methods in Enzymology* 130, 290-311
41. Surewicz, W. K., Mantsch, H. A., and Chapman, D. (1993) *Biochemistry* 32, 389-394
42. Misra, J., Schmitt, W., Hwang, D., Hsiao, L. L., Gullans, S., and Stephanopoulos, G. (2002) *Genome Res* 12, 1112-1120
43. Paschou, P., Ziv, E., Burchard, E. G., Choudhry, S., Rodriguez-Cintron, W., Mahoney, M. W., and Drineas, P. (2007) *PLoS Genet* 3, 1672-1686
44. Bylesjo, M., Eriksson, D., Kusano, M., Moritz, T., and Trygg, J. (2007) *Plant J* 52, 1181-1191
45. Lin, Z., and Altman, R. B. (2004) *Am J Hum Genet* 75, 850-861
46. Beckwith-Hall, B. M., Nicholson, J. K., Nicholls, A. W., Foxall, P. J., Lindon, J. C., Connor, S. C., Abdi, M., Connelly, J., and Holmes, E. (1998) *Chem Res Toxicol* 11, 260-272
47. Dupuy, A., and Simon, R. M. (2007) *J Natl Cancer Inst* 99, 147-157
48. Kabsch, W., and Sander, C. (1983) *Biopolymers* 22, 2577-2637
49. Krimm, S., and Bandekar, J. (1986) Vibrational spectroscopy and conformation of peptides, polypeptides, and proteins. in *Advances in Protein Chemistry* (Anfinsen, C. B., Edsall, J. T., and Richards, F. M. eds.), Academic Press, New York. pp 181-364
50. Rath, A., Glibowicka, M., Nadeau, V. G., Chen, G., and Deber, C. M. (2009) *Proceedings of the National Academy of Sciences of the United States of America* 106, 1760-1765
51. Jin, M., Song, G., Carman, C. V., Kim, Y. S., Astrof, N. S., Shimaoka, M., Wittrup, D. K., and Springer, T. A. (2006) *Proceedings of the National Academy of Sciences of the United States of America* 103, 5758-5763
52. Hirose, K., Akimaru, E., Akiba, T., Endow, S. A., and Amos, L. A. (2006) *Mol Cell* 23, 913-923
53. Coureux, P. D., Wells, A. L., Menetrey, J., Yengo, C. M., Morris, C. A., Sweeney, H. L., and Houdusse, A. (2003) *Nature* 425, 419-423
54. Reubold, T. F., Eschenburg, S., Becker, A., Kull, F. J., and Manstein, D. J. (2003) *Nature structural biology* 10, 826-830
55. Pasinelli, P & Brown, R. (2006) *Nature Reviews Neuroscience* 7, 710-723.
56. Schiffman, D., Shasman, D. I., Zee, R., Iakoubova, O., Louie, J., Devlin, J., and Ridker, P. (2008) *Journal of the American College of Cardiology* 51, 444-448
57. Iakoubova, O., Sabatine, M., Rowland, C., Rong, C., Catanese, J., Ranade, K., Simonsen, Kirchgessner, R., Cannon, C., Devlin, J., Braunwald, E. (2008) *Journal of the American College of Cardiology* 51, 449-455
58. Iakoubova, O., Tong, C., Rowland, C., Kirchgessner, T., Young, B., Arellano, A., Shiffman, D., Sabatine, M., Campos, H., Packard, C., Pfeffer, M., White, T., Braunwald, E., Shepherd, J., Devlin, J., Sacks, F. (2008) *Journal of the American College of Cardiology* 51, 435-443
59. Chene, P. (2002) *Nature Reviews, Drug Discovery* 1, 665-673
60. Hochhaus, A., Kreil, S., Corbin, A. S., La Rosee, P., Muller, M. C., Lahaye, T., Hanfstein, B., Schoch, C., Cross, N. C. P., Berger, U., Gschaidmeier, H., Druker, B. J., and Hehlmann, R. (2002) *Leukemia* 16, 2190-96
61. Shah, N. P., Nicoll, J. M., Nagar, B., Gorre, M. E., Paquette, R. L., Kuriyan, J., and Sawyers, C. L. (2002) *Cancer Cell* 2, 117-125
62. Carter, B. Z., Mak, D. H., Shi, Y., Schober, W. D., Wang, R.-Y., Konopleva, M., Koller, E., Dean, N. M., and Andreeff, M. (2006) *Cell Cycle* 5, 2223-2229

The complete disclosures of all references cited in this specification are hereby incorporated by reference. Also incorporated by reference are the complete disclosures of the following: Provisional application No. 61/154,121, filed Feb. 20, 2009, entitled "Protein Structural Biomarkers to Guide Targeted Chemotherapies"; Provisional application No. 61/261,939, filed Nov. 17, 2009, entitled "Protein Structural Biomarkers to Guide Targeted Chemotherapies"; R. Buckley et al., "Conformational specificity in allosteric signaling: high-throughput measurement of modular secondary structural changes within human Eg5 kinesin," an abstract submitted to the Biophysical Society 53rd Annual Meeting published online February 2009; B. Jun and S. Kim, "Millisecond time-lapsed monitoring of ATP hydrolysis by human Eg5 kinesin: real-time dynamics of conformation and chemistry in vitro," an abstract submitted to the Biophysical Society 53$^{rd}$ Annual Meeting published online February 2009; C. L. Parke et al., "Crystal structure of HsEg5 in complex with S-trityl-L-cysteine," an abstract submitted to the Biophysical Society 53$^{rd}$ Annual Meeting published online by February 2009; E. D. Kim et al., "Allosteric drug discrimination is coupled to mechanochemical changes in the Kinesin-5 motor core," a manuscript accepted by the Journal of Biological Chemistry in February 2010; and B. Jun and S. Kim, "Real-Time structural transitions are coupled to chemical steps in ATP hydrolysis by Eg5 kinesin," a manuscript accepted by the Journal of Biological Chemistry in February 2010. In the event of an otherwise irreconcilable conflict, however, the present specification shall control.

What is claimed:

1. An in vitro analytical method for determining the response of one or more polymorphic variants x of a protein from a patient to a drug compound, wherein the drug compound inhibits at least one polymorphic variant y of the protein, said method comprising the steps of:
   (a) measuring the conformation of each polymorphic variant x in the absence of drug compound, of polymorphic variant y in the absence of drug compound, and of polymorphic variant y when bound to the drug compound by vibrational spectroscopy using a spectrometer;
   (b) determining whether the vibrational spectrum in an amide I region of each polymorphic variant x directly overlays onto the amide I band frequency when superimposed to: (i) the vibrational spectrum of polymorphic variant y, in the absence of the drug compound, or (ii) the vibrational spectrum of polymorphic variant y when bound to the drug compound;
   (c) resolving whether each of one or more polymorphic variants x: (i) will not be resistant to the therapeutic effect of the drug compound if the vibrational spectrum in the amide I region directly overlays onto the amide I band frequency when superimposed to the vibrational spectrum of polymorphic variant y, in the absence of the drug compound; or (ii) will be resistant to the therapeutic effect of the drug compound if the vibrational spectrum in the amide I region directly overlays onto the amide I band frequency when superimposed to the vibrational spectrum of polymorphic variant y, when bound to the drug compound; and
   (d) administering to the patient an effective amount of the drug compound identified in step (c)(i),
wherein the vibrational spectroscopic spectrum in the amide I region is determined as absorption or transmittance at one or more wavelengths.

2. The method of claim 1, wherein step (a) is conducted by infrared or Raman spectroscopic measurement.

3. The method of claim 1, wherein step (a) is conducted by Fourier-transform infrared spectroscopy.

4. The method of claim 1, wherein the drug compound is a chemotherapeutic agent.

5. The method of claim 4, wherein the drug compound is a chemotherapeutic agent that acts as an allosteric inhibitor of the protein.

6. The method of claim 5, wherein the drug compound inhibits mitosis.

7. The method of claim 1, wherein the protein is an ATPase.

8. The method of claim 1, wherein the ATPase is selected from the group consisting of muscle myosin II, $Na^+,K^+$-ATPase, P glycoprotein, $H^+,K^+$-pump, vacuolar $H^+$-ATPase, and DNA topoisomerase II.

9. The method of claim 1, wherein the protein is a kinesin selected from the group consisting of Eg5, Kif5A, Kif21A, Kif1B, and Kif6.

10. The method of claim 1, wherein the protein is kinesin Eg5, and wherein the drug compound inhibits kinesin Eg5.

11. The method of claim 10, wherein the drug is selected from the group consisting of monastrol, S-trityl-L-cysteine and its derivatives, quinazolines (e.g., ispinesib), adociasulfates, thetrahydroishquinolines, dihydropyrazoles, thiophenes, pyrrolotriazines, thiazoles, gossypol, indoles, and biphenyls.

12. The method of claim 10, wherein the drug is monastrol.

13. The method of claim 10, wherein the drug is S-trityl-L-cysteine.

14. The method of claim 1, wherein the protein is the tyrosine kinase BCR-ABL.

15. The method of claim 14, wherein the drug is Gleevec.

16. The method of claim 1, wherein one or more polymorphic variants x have an amino acid sequence or a DNA sequence different than polymorphic variant y.

17. The method of claim 1, wherein the polymorphic variants of the protein are found in a human population.

18. The method of claim 1, wherein at least one polymorphic variant x of the protein or the DNA sequence encoding the polymorphic variant x of the protein is isolated from a human patient sample and wherein the responsiveness of polymorphic variant x to the drug compound is used to predict the responsiveness of the human patient to the drug compound.

19. The method of claim 1, wherein the protein is a drug target for a disease.

20. The method of claim 19, wherein the protein is the drug target for the drug compound.

21. An in vitro analytical method for determining the response of a patient to a drug compound, wherein the patient has a disease, wherein the drug compound is therapeutically effective in patient populations with the disease, and wherein the protein is polymorphic in the population, said method comprising the steps of:
   (a) measuring the conformation of the polymorphic variant of the protein isolated from the patient (variant x) in the absence of the drug compound, of a polymorphic variant of the protein that is known to be responsive to the drug compound (variant y) in the absence of drug compound, and of polymorphic variant y when bound to the drug compound by vibrational spectroscopy using a spectrometer;
   (b) determining whether the vibrational spectrum in an amide I region of polymorphic variant x directly overlays onto the amide I band frequency when superimposed to: (i) the vibrational spectrum of polymorphic variant y in the absence of the drug compound, or (ii) the vibrational spectrum of polymorphic variant y when bound to the drug compound;
   (c) resolving whether the patient (i) will not be resistant to the therapeutic effect of the drug compound if the vibrational spectrum in the amide I region of polymorphic variant x directly overlays onto the amide I band frequency when superimposed to the vibrational spectrum of polymorphic variant y, in the absence of the drug compound; or (ii) will be resistant to the therapeutic effect of the drug compound if the vibrational spectrum in the amide I region of polymorphic variant x directly overlays onto the amide I band frequency when superimposed to the vibrational spectrum of polymorphic variant y, when bound to the drug compound; and (d) administering to the patient an effective amount of the drug compound identified in step (c)(i),
wherein the vibrational spectroscopic spectrum in the amide I region is determined as absorption or transmittance at one or more wavelengths.

* * * * *